US 9,428,815 B2

(12) United States Patent
Schinazi

(10) Patent No.: US 9,428,815 B2
(45) Date of Patent: Aug. 30, 2016

(54) HIV-1 REVERSE TRANSCRIPTASE CODON DELETION AND ITS USE IN THE MANAGEMENT AND TREATMENT OF HIV INFECTIONS

(75) Inventor: Raymond F. Schinazi, Atlanta, GA (US)

(73) Assignee: Emory University, Atlanta, GA (US)

(*) Notice: Subject to any disclaimer, the term of this patent is extended or adjusted under 35 U.S.C. 154(b) by 888 days.

(21) Appl. No.: 12/595,358

(22) PCT Filed: Apr. 10, 2008

(86) PCT No.: PCT/US2008/004666
§ 371 (c)(1),
(2), (4) Date: Oct. 21, 2009

(87) PCT Pub. No.: WO2008/124192
PCT Pub. Date: Oct. 16, 2008

(65) Prior Publication Data
US 2010/0130381 A1    May 27, 2010

Related U.S. Application Data

(60) Provisional application No. 60/922,838, filed on Apr. 10, 2007.

(51) Int. Cl.
| | | |
|---|---|---|
| *C12Q 1/70* | (2006.01) | |
| *C12Q 1/68* | (2006.01) | |
| *C07H 21/00* | (2006.01) | |
| *C12N 7/00* | (2006.01) | |
| *C12P 19/34* | (2006.01) | |
| *C12N 9/12* | (2006.01) | |
| *G06F 19/18* | (2011.01) | |
| *G06F 19/28* | (2011.01) | |

(52) U.S. Cl.
CPC ............. *C12Q 1/703* (2013.01); *C12N 9/1276* (2013.01); *G06F 19/18* (2013.01); *G06F 19/28* (2013.01); *Y10S 435/911* (2013.01)

(58) Field of Classification Search
CPC ...... C12Q 1/703; C12N 9/1276; G06F 19/18
USPC .......................................................... 435/5
See application file for complete search history.

(56) References Cited

U.S. PATENT DOCUMENTS

| | | | |
|---|---|---|---|
| 5,703,058 A | 12/1997 | Schinazi et al. | |
| 5,905,070 A | 5/1999 | Schinazi et al. | |
| 7,115,584 B2 | 10/2006 | Schinazi et al. | |
| 7,655,785 B1* | 2/2010 | Bentwich | 536/24.1 |
| 2005/0239053 A1* | 10/2005 | Azijn et al. | 435/5 |
| 2006/0094020 A1* | 5/2006 | Parkin et al. | 435/6 |

FOREIGN PATENT DOCUMENTS

| | | |
|---|---|---|
| EP | 0 409 227 | 7/1990 |
| WO | WO 93/07259 | 4/1993 |
| WO | WO9307259 | * 4/1993 |

OTHER PUBLICATIONS

Zhang et al., 2006, Novel Nonnucleoside Inhibitors that Select Nucleoside Inhibitor Resistance Mutations in Human Immunodeficiency Virus Type 1 Reverse Transcriptase, Antimicrobial Agents and Chemotherapy, 50(8): 2772-2781.*
Winters et al. 2000, Genotypic, Phenotypic, and Modeling Studies of a Deletion in the b3-b4 Region of the Human Immunodeficiency Virus Type 1 Reverse Transcriptase Gene that is Associated with Resistance to Nucleoside Reverse Transcriptase Inhibitors, Journal of Virology, 74(22): 10707-10713.*
Masquelier et al., 2001, Genotypic and Phenotypic Resistance Patterns of Human Immunodeficiency Virus Type I Variants with Insertions or Deletions in the Reverse Transcriptase (RT): Multicenter Study of Patients Treated with RT inhibitors, Antimicrobial Agents and Chemotherapy, 45(6): 1836-1842.*
Villena et al., 2007, Relative Fitness and Replication Capacity of a Multinucleoside Analogue-Resistant Clinical Human Immunodeficiency Virus Type I Isolate with a Deletion of Codon 69 in the Reverse Transcriptase Coding Region, Journal of Virology, 81(9): 4713-4721.*
Preston et al., 1988, Fidelity of HIV-1 Reverse Transcriptase, Science, 242: 1168-1171.*
Boyer et al., "Effects of the Δ67 Complex of Mutations in Human Immunodeficiency Virus Type 1 Reverse Transcriptase on Nucleoside Analog Excision." *Journal of Virology* 78(18): 9987-9997 (2004).
Chu et al., "Anti-HIV Activity of (−)-(2R, 4R)-1-(2-Hydroxymethyl-1,3-dioxolan-4-yl)thymine against drug resistant HIV-1 mutants and studies of its molecular mechanism." *J. Med. Chem.* 48: 3949-3952 (2005).
Fitzgibbon et al., "Human immunodeficiency virus type 1 pol gene mutations which cause decreased susceptibility to 2',3'-dideoxycytidine." *Antimicrob. Agents Chemother.* 36(1): 153-157 (1992).
Garcia-Lerma et al., "Evidence of a role for the Q151L mutation and the viral background in development of multiple dideoxynucleoside-resistant human immunodeficiency virus type 1." *Journal of Virology* 74(20): 9339-9346 (2000).

(Continued)

*Primary Examiner* — Janet L Andres
*Assistant Examiner* — Barry A Chestnut
(74) *Attorney, Agent, or Firm* — Kilpatrick Townsend & Stockton, LLP

(57) ABSTRACT

The present invention provides an isolated HIV-1 mutant and isolated nucleic acid molecules comprising HIV-RT coding sequences harboring a novel mutation in the S68 codon, and in particular, deletions of the S68 codon. This novel deletion reduces the sensitivity of HIV to various nucleoside reverse transcriptase inhibitors. Methods of using this mutation for selecting effective antiretroviral agents in vitro and in vivo, methods for monitoring infection progression in HIV-infected individuals and methods for avoiding the emergence of and/or to treat individuals infected with HIV comprising mutations, including deletions, at the S68 codon of HIV-RT are provided.

3 Claims, 6 Drawing Sheets

(56) References Cited

OTHER PUBLICATIONS

Hammond et al., "In Vitro Selection and Analysis of Human Immunodeficiency Virus Type 1 Resistant to Derivatives of β-2',3'-Didehydro-2',3'-Dideoxy-5-Fluorocytidine." *Antimicrob. Agents Chemother.* 49(9): 3930-3932 (2005).

Hu et al., "Virologic Characterization of HIV Type 1 With a Codon 70 Deletion in Reverse Transcriptase." *J. Acquir. Immune Defic. Syndr.*, 45: 494-500 (2007).

Imamichi et al., "High-Level Resistance to 3'-Azido-3'-Deoxythimidine due to a Deletion in the Reverse Transcriptase Gene of Human Immunodeficiency Virus Type 1." *Journal of Virology* 74(2): 1023-1028 (2000).

Imamichi et al., "Relative Replication Fitness of a High-Level 3'-Azido-3'-Deoxythymidine-Resistant Variant of Human Immunodeficiency Virus Type 1 Possessing an Amino Acid Deletion at Codon 67 and a Novel Substitution (Thr→ Gly) at Codon 69." *Journal of Virology* 74(23): 10958-10964 (2000).

Larder et al., "HIV with Reduced Sensitivity to Zidovudine (AZT) Isolated during Prolonged Therapy." *Science* 243: 1731-1734 (1989).

Lennerstrand et al., "Biochemical Studies on the Mechanism of Human Immunodeficiency Virus Type 1 Reverse Transcriptase Resistance to 1-(β-D-Dioxolane) Thymine Triphosphate." *Antimicrobial Agents and Chemotherapy* 51(6): 2078-2084 (2007).

Ludwig et al., "Rapid and efficient synthesis of nucleoside 5'-O-(1-thiotriphosphates), 5'-triphosphates and 2',3'-cyclophosphorothioates using 2-chloro-4H-1,3,2-benzodioxaphosphorin-4-one." *Journal of Organic Chemistry* 54: 631-635 (1989).

Mellors et al., "In vitro selection and molecular characterization of human immunodeficiency virus-1 resistant to non-nucleoside inhibitors of reverse transcriptase." *Molecular Pharmacology* 41: 446-451 (1992).

Nunberg et al., "Viral Resistance to Human Immunodeficiency Virus Type 1-Specific Pyridinone Reverse Transcriptase Inhibitors." *Journal of Virology*, 65(9): 4887-4892 (1991).

Richman et al., "Human immundodeficiency virus type 1 mutants resistance to nonnucleoside inhibitors of reverse transcriptase arise in tissue culture." *Proc. Natl. Acad. Sci. USA*, 88: 11241-11245 (1991).

Richman, D.D., "Loss of nevirapine activity associated with the emergence of resistance in clinical trials. The ACTG Study Team." Abstract. *Int Conf AIDS* 8(2): B183 (1992).

Saag et al., "A Short-Term Clinical Evaluation of L-697,661, a Non-Nucleoside Inhibitor of HIV-1 Reverse Transcriptase". *N Engl J Med* 329:1065-1072 (1993).

Schmit et al., "Multiple dideoxynucleoside analogue-resistant (MddNR) HIV-1 strains isolated from patients from different European countries." *AIDS* 12(15): 2005-2015 (1998).

Schinazi et al., "Activities of 3'-Azido-3'-Deoxythymidine Nucleotide Dimers in Primary Lymphocytes Infected with Human Immunodeficiency Virus Type 1." *Antimicrobial Agents and Chemotherapy* 34(6): 1061-1067 (1990).

Schinazi et al., "Mutations in retroviral genes associated with drug resistance: 2000-2001 update." *Int Antiviral News* 8: 65-91 (2000).

Schinazi et al., "Pharmacology of current and promising nucleosides for the treatment of human immunodeficiency viruses." *Antiviral Research* 71: 322-334 (2006).

St. Clair et al., "Resistance to ddI and sensitivity to AZT induced by a mutation in HIV-1 reverse transcriptase." *Science* 253(5027): 1557-1559 (1991).

Stuyver et al., "Antiviral Activities and Cellular Toxicities of Modified 2',3'-Dideoxy-2',3'-Didehydrocytidine Analogues." *Antimicrobial Agents and Chemotherapy* 46(12): 3854-3860 (2002).

Tamalet et al., "Multidrug resistance genotypes (insertions in the β3-β4 finger subdomain and MDR mutations) of HIV-1 reverse transcriptase from extensively treated patients: incidence and association with other resistance mutations." *Virology* 270: 310-316 (2000).

Winters et al., "Genotypic, phenotypic, and modeling studies of a deletion in the β3-β4 region of the human immunodeficiency virus type 1 reverse transcriptase gene that is associated with resistance to nucleoside reverse transcriptase inhibitors." *Journal of Virology* 74(22): 10707-10713 (2000).

Zhang et al., "Novel nonnucleoside inhibitors that select nucleoside inhibitor resistance mutations in human immunodeficiency virus type 1 reverse transcriptase." *Antimicrobial Agents and Chemotherapy* 50(8): 2772-2781 (2006).

International Search Report mailed Oct. 13, 2008 in counterpart International Application No. PCT/US2008/004666.

European Nucleotide Archive, EMBL-Bank AF311157.1, website accessed Oct. 11, 2012, 3 pages.

Canadian Patent Application No. 2,684,061, Office Action, issued Mar. 10, 2014, 5 pages.

U.S. Appl. No. 13/672,761, Final Office Action, mailed Sep. 25, 2015.

\* cited by examiner

SEQUENCE LISTING

<160> NUMBER OF SEQ ID NOS: 19

<210> SEQ ID NO 1
<211> LENGTH: 28
<212> TYPE: DNA
<213> ORGANISM: Artificial Sequence
<220> FEATURE:
<221> NAME/KEY: source
<223> OTHER INFORMATION: Synthetic primer

<400> SEQUENCE: 1
ataatccacc tatcccagta ggagaaat                                28

<210> SEQ ID NO 2
<211> LENGTH: 28
<212> TYPE: DNA
<213> ORGANISM: Artificial Sequence
<220> FEATURE:
<221> NAME/KEY: source
<223> OTHER INFORMATION: Synthetic primer

<400> SEQUENCE: 2
tttggtcctt gtcttatgtc cagaatgc                                28

<210> SEQ ID NO 3
<211> LENGTH: 35
<212> TYPE: DNA
<213> ORGANISM: Artificial Sequence
<220> FEATURE:
<221> NAME/KEY: source
<223> OTHER INFORMATION: Synthetic probe

```
<400> SEQUENCE: 3
atcctgggat taaataaaat agtaagaatg tatag                          35

<210> SEQ ID NO 4
<211> LENGTH: 25
<212> TYPE: DNA
<213> ORGANISM: Artificial Sequence
<220> FEATURE:
<221> NAME/KEY: source
<223> OTHER INFORMATION: Synthetic primer

<400> SEQUENCE: 4
ttgactcaga ttggttgcac tttaa                                     25

<210> SEQ ID NO 5
<211> LENGTH: 25
<212> TYPE: DNA
<213> ORGANISM: Artificial Sequence
<220> FEATURE:
<221> NAME/KEY: source
<223> OTHER INFORMATION: Synthetic primer

<400> SEQUENCE: 5
aagaacccat agtaggagca gaaac                                     25

<210> SEQ ID NO 6
<211> LENGTH: 9
<212> TYPE: DNA
<213> ORGANISM: Human immunodeficiency virus type 1

<400> SEQUENCE: 6 gacagtact                                                        9

<210> SEQ ID NO 7
<211> LENGTH: 9
<212> TYPE: DNA
<213> ORGANISM: Human immunodeficiency virus type 1

<400> SEQUENCE: 7 gacactaaa                                                        9

<210> SEQ ID NO 8
<211> LENGTH: 68
<212> TYPE: DNA
<213> ORGANISM: Artificial Sequence
<220> FEATURE:
<221> NAME/KEY: source
<223> OTHER INFORMATION: Synthetic primer

<400> SEQUENCE: 8
caatactcca gtatttgcca taagaaaaa agacactaaa tggagaaaat tagtagattt   60
cagagaac                                                         68

<210> SEQ ID NO 9
<211> LENGTH: 68
<212> TYPE: DNA
<213> ORGANISM: Artificial Sequence
<220> FEATURE:
<221> NAME/KEY: source
<223> OTHER INFORMATION: Synthetic primer

<400> SEQUENCE: 9
gttctctgaa atctactaat tttctccatt tagtgtcttt tttctttatg gcaaatactg   60
gagtattg                                                         68
```

```
<210> SEQ ID NO 10
<211> LENGTH: 39
<212> TYPE: DNA
<213> ORGANISM: Artificial Sequence
<220> FEATURE:
<221> NAME/KEY: source
<223> OTHER INFORMATION: Synthetic primer

<400> SEQUENCE: 10
cgcgcccatg gtgcccatta gtcctattga gactgtacc                              39

<210> SEQ ID NO 11
<211> LENGTH: 39
<212> TYPE: DNA
<213> ORGANISM: Artificial Sequence
<220> FEATURE:
<221> NAME/KEY: source
<223> OTHER INFORMATION: Synthetic primer

<400> SEQUENCE: 11
gcgcgcagat cttagtactt tcctgattcc agcactgac                              39

<210> SEQ ID NO 12
<211> LENGTH: 10
<212> TYPE: PRT
<213> ORGANISM: Human immunodeficiency virus type 1

<400> SEQUENCE: 12

Ile Lys Lys Lys Asp Thr Lys Trp Arg Lys
 1               5                  10

<210> SEQ ID NO 13
<211> LENGTH: 10
<212> TYPE: PRT
<213> ORGANISM: Human immunodeficiency virus type 1

<400> SEQUENCE: 13

Ile Lys Lys Lys Ser Gly Arg Trp Arg Lys
 1               5                  10

<210> SEQ ID NO 14
<211> LENGTH: 10
<212> TYPE: PRT
<213> ORGANISM: Human immunodeficiency virus type 1

<400> SEQUENCE: 14

Ile Lys Lys Lys Asp Asn Thr Trp Arg Lys
 1               5                  10

<210> SEQ ID NO 15
<211> LENGTH: 10
<212> TYPE: PRT
<213> ORGANISM: Human immunodeficiency virus type 1

<400> SEQUENCE: 15

Ile Lys Lys Lys Asp Gly Thr Trp Arg Lys
 1               5                  10

<210> SEQ ID NO 16
<211> LENGTH: 10
<212> TYPE: PRT
<213> ORGANISM: Human immunodeficiency virus type 1

<400> SEQUENCE: 16

Ile Lys Lys Lys Ser Gly Lys Trp Arg Lys
 1               5                  10
```

```
<210> SEQ ID NO 17
<211> LENGTH: 10
<212> TYPE: PRT
<213> ORGANISM: Human immunodeficiency virus type 1

<400> SEQUENCE: 17

Ile Lys Lys Lys Asp Gly Gly Trp Arg Lys
 1               5                   10

<210> SEQ ID NO 18
<211> LENGTH: 11
<212> TYPE: PRT
<213> ORGANISM: Human immunodeficiency virus type 1

<400> SEQUENCE: 18

Ile Lys Lys Lys Asp Ser Thr Lys Trp Arg Lys
 1               5                   10

<210> SEQ ID NO 19
<211> LENGTH: 11
<212> TYPE: PRT
<213> ORGANISM: Human immunodeficiency virus type 1

<400> SEQUENCE: 19

Ile Lys Lys Lys Asp Ser Thr Lys Trp Arg Lys
 1               5                   10
```

HIV-1 REVERSE TRANSCRIPTASE CODON DELETION AND ITS USE IN THE MANAGEMENT AND TREATMENT OF HIV INFECTIONS

This application is a national stage entry of PCT/US2008/004666, filed Apr. 10, 2008, which claims priority from U.S. Provisional Patent Application No. 60/922,838, filed Apr. 10, 2007, the contents of which are hereby incorporated by reference in its entirety.

STATEMENT REGARDING FEDERALLY FUNDED RESEARCH

This invention was made with government support under Grant No. 5R37-AI-41980 awarded by the National Institutes of Health. The government has certain rights in the invention.

BACKGROUND OF THE INVENTION

In 1983, the etiological cause of AIDS was determined to be the human immunodeficiency virus (HIV). In 1985, it was reported that the synthetic nucleoside 3'-azido-3'-deoxythymidine (Zidovudine, AZT, ZDV) inhibits the replication of human immunodeficiency virus by inhibiting in its 5'-triphosphate form the HIV-1 reverse transcriptase (HIV-RT). HIV-RT is active early in the viral replication cycle and is necessary for continued viral replication. Currently, a total eight synthetic nucleosides have been approved by the US FDA. These are: AZT (mentioned above), 2',3'-dideoxyinosine (Videx, DDI), 2',3'-dideoxycytidine (DDC), 2',3'-dideoxy-2',3'-didehydrothymidine (stavudine, D4T), cis-2-hydroxymethyl-5-(5-fluorocytosin-1-yl)-1,3-oxathiolane (emtricitabine, FTC), (−)-cis-2-hydroxymethyl-5-(cytosin-1-yl)-1,3-oxathiolane (Lamivudine, 3TC), (1S,4R)-4-[2-amino-6-(cyclopropyl-amino)-9H-purin-9-yl]-2-cyclopentene-1-methanol succinate (abacavir, ABC), and the acyclic nucleotide 9-[(R)-2-[[bis[[(isopropoxycarbonyl)oxy]methoxy]phosphinyl]methoxy]propyl]adenine fumarate (tenofovir-DF, TDF). All nucleoside reverse transcriptase inhibitors (NRTI) require phosphorylation to their triphosphate (TP) forms, while metabolic activation of tenofovir requires phosphorylation to its 12 diphosphate (tenofovir-DP). Such so-called NRTI mimic natural nucleosides in the cell. After cellular phosphorylation to the 5'-triphosphate by cellular kinases, these synthetic nucleosides can be incorporated into a growing strand of viral DNA, causing chain termination due to the absence of the 3'-hydroxyl group found in natural nucleosides that are used in the DNA chain elongation reaction catalyzed by HIV-RT. NRTI therapies in HIV treatment are reviewed in Schinazi et al., *Antiviral Research* 71:322-334 (2006)).

HIV shows high genetic variability in part as a result of its fast viral replication cycle coupled with the high mutation rate of and active recombinogenic characteristics of HIV-RT, especially during viral replication in single cells co-infected by multiple different strains of HIV. Drug-resistant variants of HIV can emerge after treatment with an antiviral agent. Drug resistance most typically occurs by mutation of a gene that encodes for an enzyme used in viral replication, and most typically in the case of HIV, reverse transcriptase, protease, or DNA polymerase. NRTI treatment of HIV-1 infected individuals often leads to the emergence of mutations in the reverse transcriptase (RT). Less frequently seen are codon insertions or deletions, either which add or subtract three nucleotides and leave other codons in the correct coding frame. Codon insertions (ins) and deletions (del) have been associated with multi-drug resistance (MDR) in clinical samples obtained from HIV-1 infected individuals treated with antiretroviral agents (67del, 69del, 69ins, 70del).

The β3-β4 hairpin loop of the finger domain of RT is thought to be directly involved in the interaction of the enzyme with its substrates (the template-primer complex and the dNTP) (Tamalet et al., *Virol.* 270:310-316 (2000)). Genetic rearrangements in the β3-β4 loop have been found in patients extensively treated with anti-HIV drugs and experiencing therapeutic failure (Tamalet, supra; Winters et al., *J. Virol.* 74(22):10707-10713 (2000)).

The efficacy of a drug against HIV infection can be prolonged, augmented, or restored by administering the compound in combination or alternation with a second, and in particular a third, antiviral compound that induces a different mutation from that caused by the principle drug. Alternatively, the pharmacokinetics, biodistribution, or other parameter of the drug can be altered by such combination or alternation therapy, although this is not recommended for HIV infections. In general, combination therapy is typically preferred over alternation therapy because it induces multiple simultaneous pressures on the virus. One cannot predict, however, what mutations will be induced in the HIV-1 genome by a given new drug, whether the mutation is permanent or transient, or how an infected cell with a mutated HIV-1 sequence will respond to therapy with other agents in combination or alternation. This is exacerbated by the fact that there is a paucity of data on the kinetics of drug resistance in long-term cell cultures treated with modern antiretroviral agents.

HIV-1 variants resistant to AZT, DDI, 3TC, D4T, DDC, ABC or TDF have been isolated from patients receiving long term monotherapy with these drugs (Larder et al., *Science* 1989; 243:1731-4; St. Clair et al., *Science* 1991; 253:1557-9; and Fitzgibbon et al., *Antimicrob. Agents Chemother.* 1992; 36:153-7; Schinazi, et al., *Intl. Antiviral News* 2000; 8:65-92). Mounting clinical evidence indicates that AZT and 3TC resistance is a predictor of poor clinical outcome in both children and adults. The rapid development of HIV-1 resistance to non-nucleoside reverse transcriptase inhibitors (NNRTI) has also been reported both in cell culture and in human clinical trials (Nunberg et al. *J. Virol.* 1991; 65(9):4887-92; Richman et al., *Proc Natl Acad Sci* (*USA*) 1991; 88:11241-5; Mellors et al., *Mol. Pharm.* 1992; 41:446-51; Richman D D and the ACTG 164/168 Study Team. Second International HIV-1 Drug Resistance Workshop. (Noordwijk, the Netherlands. 1993); and Saag et al., *N Engl J Med* 1993; 329:1065-1072). In the case of the NNRTI L'697,661, drug-resistant HIV-1 emerged within 2-6 weeks of initiating therapy in association with the return of viremia to pretreatment levels. (Saag et al., supra). Breakthrough viremia associated with the appearance of drug-resistant strains has also been noted with other classes of HIV-1 inhibitors, including protease, fusion and integrase inhibitors. This experience has led to the realization that the potential for HIV-1 drug resistance must be assessed early on in the preclinical evaluation of all new therapies for HIV-1.

The emergence of resistant HIV strains during viral therapy has presented a major challenge to delay, prevent or attenuate the onset of resistance. Common resistance mutations, including thymidine associated mutations (TAM), K65R and M184V are problematic in HIV drug development. Mutations observed to emerge following exposure to various NRTI are summarized in Schinazi et al., supra, 2006 (see Table 1). Novel NRTI are under pre-clinical development that are good substrates for cellular kinases, have high bioavailability (especially oral), reduced toxicity and significant levels of activity against the commonly found NRTI-resistant HIV-1 mutants, such as D67N, K70R, T215Y, K219Q, K65R and M184V (Chu et al., *J. Med. Chem.* 48:3949-3952 (2005)).

2',3'-Dideoxy-2',3'-didehydro-5-fluoro-cytidine (D4FC, DFC; dexelvucitabine) is a known NRTI compound (see, e.g., EP 0 409 227 A2, U.S. Pat. Nos. 5,703,058 and 5,905,070). Treatment with β-L-D4FC rapidly selects for a mutation at codon 184 (methionine to valine) of the reverse transcriptase region of the virus, resulting in a high level of resistance to 3TC and FTC. β-D-D4FC, in contrast, is not significantly cross-resistant to AZT, DDC, DDI, D4T, 3TC, (−)-FTC or β-L-D4FC. β-D-D4FC treatment selects for HIV-1 variants having mutations at codons I63L, K65R, K70N, K70E, or R172K of the HIV-RT region of the virus (see also Hammond et al., *Antimicrob. Agents Chemother.* 49(9):3930-3932 (2005)). Thus, β-D-D4FC can be used generally as salvage therapy for any HIV-infected individual that exhibits resistance to other anti-HIV agents whose drug resistance patterns correlate with mutations at codons different from those selected by β-D-D4FC treatment. Based on this, methods for treating HIV have been reported that involve administering β-D-D4FC or its pharmaceutically acceptable salt or prodrug in combination or alternation with a drug that selects for variants having one or more mutations in HIV-1 at a location other than codons I63L, K65R, K70N, K70E, or R172K (U.S. Pat. No. 7,115,584, and Hammond et al.).

Current treatments for HIV infection are most often those referred to as "highly active antiretroviral therapy" or HAART and involve administering combinations ("cocktails") comprising at least three drugs—two NRTI in combination with either a protease inhibitor or a NNRTI. Results of studies on the emergence of drug resistance and correlations between antiviral drugs and mutation patterns present in selected HIV variant genes are useful in directing resistance testing of viruses from HIV-infected individuals treated with antiviral agents such as NRTI and in choosing combinations of nucleoside analogs for treatment and prevention of drug resistant HIV. Characterization of these mutations is key in determining potential cross-resistance and in HIV treatment management. It is thus desirable to understand more about NRTI resistance patterns and how they correlate with HIV genotypes and mutations in essential HIV genes, such as HIV-RT.

SUMMARY OF THE INVENTION

The present invention addresses the problems above by identifying a novel deletion in HIV-1 RT of the S68 codon ("S68del"; which may alternatively be a deletion of the AGT codon 68 trinucleotide, or of the adjacent +1 frameshift trinucleotide GTA) revealed during the selection of virus with dexelvucitabine (DFC) in primary human lymphocytes. The novel S68 deletion and the distinct multi-drug resistant phenotype it imparts on HIV may be an important variable in NRTI multidrug resistance, management of HIV-infected persons and improved treatment strategies.

The S68 deletion was investigated phenotypically against selected antiviral agents for resistance and demonstrated resistance to several clinically important NRTI. The S68del produced greater than 30-fold increased resistance to DFC, lamivudine, emtricitabine, tenofovir, abacavir and amdoxovir. As expected, the S68del demonstrated no resistance to NNRTI and protease inhibitors.

Codon 68 mutants, and S68del in particular, are expected to precede immunologic decline of an infected individual over time. Once the codon 68 mutation has been detected in plasma HIV RNA or lymphocytes of an HIV-infected individual, a specific therapeutic regimen is considered. In cases in which the HIV-infected individual is already undergoing antiretroviral therapy, an alteration in the therapeutic regimen is preferably considered.

In certain embodiments, the invention thus provides a nucleic acid molecule comprising sequences encoding part or all of HIV-1 RT, the HIV-RT sequences comprising a codon 68 mutation, provided that when the codon 68 mutation is an S68 substitution, it occurs alone or in combination with a mutation other than a K65R mutation. The invention also provides a nucleic acid molecule comprising sequences encoding part or all of HIV-1 RT, the HIV-RT sequences comprising a codon 68 mutation, wherein the codon 68 mutation is the only mutation in the HIV-RT sequences. The invention further provides a nucleic acid molecule comprising sequences encoding part or all of HIV-1 RT, the HIV-RT sequences comprising a codon 68 deletion wherein the S68 deletion removes the codon 68 AGT trinucleotide, or wherein the S68 deletion removes the GTA trinucleotide spanning codons 68 and 69. Preferably, isolated nucleic acid molecules of the invention comprise a minimum of nine, preferably of 10-25 or more nucleotides so that they may be used as selective primers, e.g., in nucleic acid amplification methods, or as probes in nucleic acid hybridization techniques.

The invention also provides an isolated HIV-1 or HIV-2 comprising any of the previously described nucleic acids.

The present invention also provides a method of evaluating the effectiveness of an antiretroviral agent or preventing or treating HIV infection of cells, comprising: (i) treating cells with an antiretroviral agent; (ii) infecting cells with an HIV-1 (or HIV-2) having a codon 68 mutation in the reverse transcriptase coding sequence, provided that when the codon 68 mutation is an S68 substitution, it is not in combination with a K65R mutation; and (iii) determining the effect of the agent on viral replication; wherein steps (i) and (ii) can be performed in any order.

In one embodiment, the invention provides a method of selecting an effective antiretroviral therapy for an HIV-infected person, the method comprising: (i) collecting a plasma sample from an HIV-infected person who is being treated with an antiretroviral agent; and (ii) determining whether the plasma sample comprises nucleic acid encoding HIV-RT sequences comprising a codon 68 mutation, provided that when the codon 68 mutation is an S68 substitution, it is not in combination with a K65R mutation. In certain embodiments, the codon 68 mutation is determined by a method comprising polymerase chain reaction. In certain of such embodiments, the polymerase chain reaction is nested. In other such embodiments, the polymerase chain reaction is real-time. In further embodiments, the method comprising polymerase chain reaction utilizes primers SK38: ATA ATC CAC CTA TCC CAG TAG GAG AAA T (SEQ ID NO: 1) and SK39: TTT GGT CCT TGT CTT ATG TCC AGA ATG C (SEQ ID NO: 2).

It may be desirable after detecting the codon 68, e.g., S68del, mutation to alter the course of the person's current treatment regimen to include one or more antiretroviral agents that are effective in inhibiting the replication of an HIV mutant comprising an S68 mutation, e.g. S68del.

In another embodiment, the invention provides a method of selecting an effective antiretroviral therapy for an HIV-infected individual, comprising: (i) collecting lymphocytic cells from an HIV-infected individual; and (ii) determining whether the cells comprise nucleic acid encoding HIV-RT sequences comprising a codon 68 mutation, wherein if HIV-RT sequences comprising a codon 68 mutation are present, an antiretroviral therapy is selected which inhibits production of HIV-RT codon 68 mutant variant RNA in the cells, provided that when the codon 68 mutation is an S68 substitution, it is not in combination with a K65R mutation.

In certain embodiments, the invention provides a method of selecting an effective antiretroviral therapy for an HIV-infected individual, comprising: (i) collecting lymphocytic cells from an HIV-infected individual; and (ii) determining whether the cells comprise nucleic acid encoding HIV-RT sequences comprising a codon 68 mutation, wherein if HIV-RT sequences comprising a codon 68 mutation are present, an antiretroviral therapy is selected which inhibits production of HIV-RT codon 68 mutant variant RNA in the cells, provided that when the codon 68 mutation is an S68 substitution, it is not in combination with a K65R mutation, wherein if the HIV-infected individual was undergoing an antiretroviral treatment prior to step (i), the treatment is altered based on the determination step (ii).

In further embodiments, the invention provides a method for evaluating the effectiveness to an HIV-infected individual of a selected antiretroviral agent or therapy, the method comprising: (i) collecting a sample from an HIV-infected individual; and (ii) determining whether the sample comprises nucleic acid encoding HIV reverse transcriptase having a mutation at codon 68, e.g., S68del, in which the presence of the mutation correlates positively with refractoriness of the individual to the selected antiretroviral therapy and, if the therapy remains unchanged, to accelerated immunologic decline of the HIV-infected individual compared to HIV-infected individuals who do not have the mutation.

In any of the above methods, the alteration of treatment may comprise administering at least one antiretroviral agent that reduces or eliminates RNA production by the HIV variant having a codon 68 mutation. In certain embodiments, the at least one antiretroviral agent is selected from a protease inhibitor, a non-nucleoside reverse transcriptase inhibitor, an HIV fusion inhibitor, an HIV integrase inhibitor, an RNAse H inhibitor, a CD4 binding inhibitor, a CXCR4 binding inhibitor and a CCR5 binding inhibitor. In certain embodiments, the at least one antiretroviral agent is selected from: AZT, DDI, DFDOC, D4T, DOT and DDC.

In any of the above methods, the absence of, or decreasing concentrations of, detectable HIV sequence correlates positively with the assessment that the antiretroviral agent is therapeutically effective in treating a codon 68, e.g., S68del, mutation. Moreover, in this method, the presence of, or increasing concentrations of, detectable HIV sequence correlates positively with the assessment that the antiretroviral agent is therapeutically ineffective and that a resistant virus has developed.

In another embodiment, the invention provides methods for evaluating the effectiveness to an HIV-infected individual of treatment with an antiretroviral agent or therapy prone to emergence of a codon 68 mutation, the method comprising (i) collecting a sample from an HIV-infected individual before treatment with a selected antiretroviral agent prone to emergence of a codon 68 mutation; (ii) collecting a sample from the HIV-infected individual after treatment with the selected antiretroviral agent; (iii) amplifying separately HIV-encoding nucleic acid in the samples from (i) and (ii) with HIV primers; (iv) comparing the HIV nucleic acid copy number in samples (i) and (ii), wherein a ratio of HIV nucleic acid copy number in samples (i) and (ii) of greater than about 2.5 to 1, 4 to 1, 5 to 1, 10 to 1 or more, correlates positively with the assessment that the selected antiretroviral agent has not selected an HIV-RT codon 68 mutation, e.g., S68del, and remains therapeutically effective. In certain embodiments, such methods may additionally or optionally (e.g., in step (iii)) comprise the use of HIV primers that can distinguish between the presence and absence of a codon 68 mutation, e.g., S68del in HIV-RT.

In certain other embodiments, the invention provides methods for evaluating the effectiveness to an HIV-infected individual of treatment with an antiretroviral agent or therapy prone to emergence of a codon 68 mutation, the method comprising: (i) collecting at least one sample from an HIV-infected individual at separate time intervals; (ii) amplifying HIV-encoding nucleic acid in the separate samples using HIV primers; (iii) measuring HIV nucleic acid copy numbers using the amplification products of step (ii); and (iv) comparing the HIV nucleic acid copy numbers in the samples collected during the course of the selected treatment; whereby a statistically significant decline in HIV nucleic acid copy numbers detected over the course of the treatment correlates positively with the assessment that the selected antiretroviral agent has not selected an HIV-RT codon 68 mutation, e.g., S68del, and remains therapeutically effective. In certain embodiments, such methods may additionally or optionally (e.g., in step (ii)) comprise the use of HIV primers that can distinguish between the presence and absence of a codon 68 mutation, e.g., S68del in HIV-RT.

In any of the above products or methods of the invention, the HIV-RT codon 68 mutation may be an S68 deletion that removes AGT or that removes the GTA trinucleotide spanning codons 68 and 69.

In certain embodiments of the present invention, the HIV specific primers used in the methods of the invention can distinguish between the presence and absence of a HIV reverse transcriptase codon 68 mutation, and more particularly, of the S68del mutation. Examples of such primers include, without limitation, SK38 Primer: ATA ATC CAC CTA TCC CAG TAG GAG AAA T (SEQ ID NO: 1) and SK39 Primer: TTT GGT CCT TGT CTT ATG TCC AGA ATG C (SEQ ID NO: 2). The presence of amplified product may also be detected with the SK19 probe: ATC CTG GGA TTA AAT AAA ATA GTA AGA ATG TAT AG (SEQ ID NO: 3). Other HIV specific primers may easily be designed by those of skill in the art that can detect and differentiate codon 68 mutations, including those that distinguish between S68 substitutions and the codon 68 deletion referred to herein as "S68del".

The present invention also provides methods for treating a person infected with HIV comprising the step of administering over time an antiviral agent that does not select for an HIV variant having a codon 68 mutation in the HIV-RT coding sequence. the codon 68 mutation is an S68 deletion that removes AGT or that removes the GTA trinucleotide spanning codons 68 and 69. In certain embodiments, the antiretroviral agent is one that is effective at inhibiting viral replication of an HIV-1 mutant comprising an S68 mutation, e.g., an S68 deletion so that viral RNA production is reduced or eliminated. In further embodiments, the antiretroviral agent is selected from an HIV protease inhibitor such as Lopinavir®; an HIV fusion inhibitor such as a CD4 binding inhibitor, a CXCR4 binding inhibitor or a CCR5 binding inhibitor such as Maraviroc; an HIV integrase inhibitor such as Raltegravir; an RNAseH inhibitor; an NNRTI such as Sustiva®. In certain embodiments, the antiretroviral agent is an NRTI that inhibits replication of an HIV-1 S68 mutant at concentrations that are no more than 5-fold (and preferably no more than 2.5-fold) higher than the concentration of the agent required to inhibit viral replication of wild-type HIV-1. In certain preferred embodiments, the antiretroviral agent is selected from: AZT, DDI, DFDOC, D4T, DOT or DDC. In yet other preferred embodiments, the antiretroviral agent is AZT. In yet other preferred embodiments, the antiretroviral agent is DDI.

In other embodiments, the invention provides a kit comprising at least one pair of primers designed to detect the presence of a codon 68 mutation in HIV-RT coding sequences. In further embodiments, the kit may be designed to detect the codon 68 deletion that removes the AGT trinucleotide encoding S68 or the GTA trinucleotide spanning codons 68 and 69. The kit may comprise at least one primer is selected from SK38 and SK39. The kit may further comprise a nucleic acid probe comprising or consisting essentially of the following nucleic acid sequence (SK19): ATC CTG GGA TTA AAT AAA ATA GTA AGA ATG TAT AG (SEQ ID NO: 3).

In certain embodiments, the invention provides a nucleic acid product of priming with primers SK38 (SEQ ID NO: 1) and SK39 (SEQ ID NO: 2), wherein the nucleic acid product comprises sequences encoding HIV-1 RT, the HIV-RT sequences comprising a codon 68 mutation, provided that when the codon 68 mutation is an S68 substitution, it is not in combination with a K65R mutation.

In other embodiments, the invention provides a nucleic acid product of priming with primers SK38 (SEQ ID NO: 1) and SK39 (SEQ ID NO: 2), wherein the nucleic acid product comprises sequences encoding HIV-1 RT, the HIV-RT sequences comprising a codon 68 mutation, wherein the codon 68 mutation is an S68 deletion that removes AGT or that removes the GTA trinucleotide spanning codons 68 and 69.

In certain embodiments, the invention provides any of the above nucleic acids or nucleic acid products attached to a solid support. In further embodiments, the invention provides an array comprising any of the above nucleic acids or nucleic acid products.

In certain embodiments, the invention provides use of an antiretroviral agent to produce a composition useful in treating a subject infected with HIV-1, wherein the antiretroviral agent is one which does not select for an HIV-1 variant comprising a codon 68 mutation in the HIV-RT coding sequence. In further embodiments, the codon 68 mutation is an S68 deletion that removes AGT or that removes the GTA trinucleotide spanning codons 68 and 69. In certain embodiments, the antiretroviral agent is selected from: a protease inhibitor, a non-nucleoside reverse transcriptase inhibitor, an HIV fusion inhibitor, an HIV integrase inhibitor, an RNAse H inhibitor, a CD4 binding inhibitor, a CXCR4 binding inhibitor and a CCR5 binding inhibitor. In further embodiments, the antiretroviral agent is selected from: AZT, DDI, DFDOC, D4T, DOT and DDC.

DETAILED DESCRIPTION OF THE INVENTION

Definitions

Figure 1:
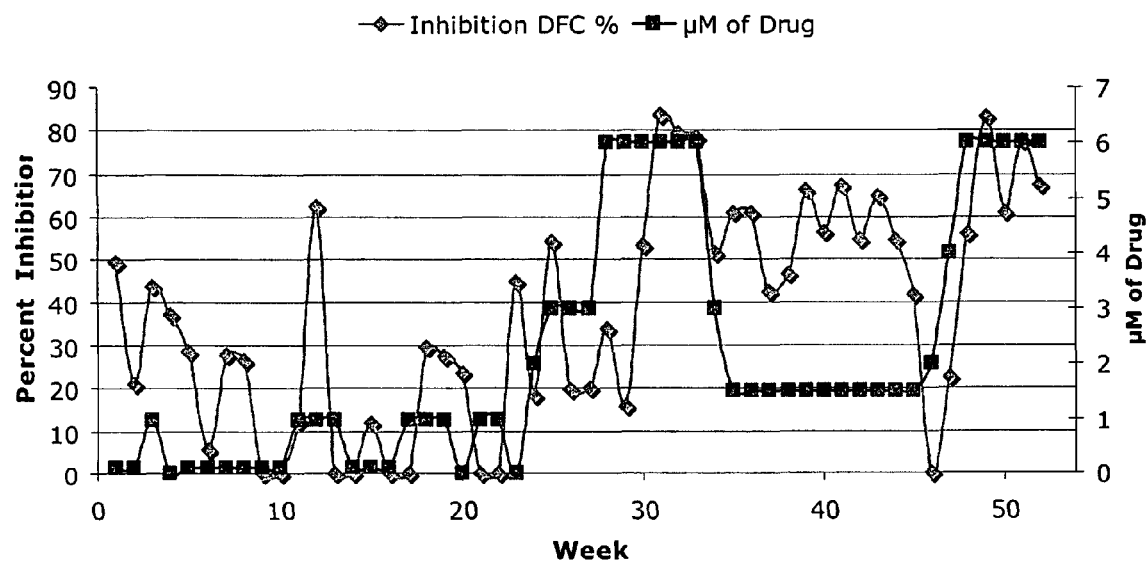
FIG. 1 is a graph showing percent inhibition by DFC (dexelvucitabine) and the amounts of DFC (in μm) used during isolation of the S68del virus.

As used herein, a "phenotypic change" in an HIV mutant is one that confers a statistically significant change in viral replication rates in the presence of a select antiviral compound or agent, defined herein to be at least a 2.5-fold, and preferably at least a 5-fold or higher increase in $EC_{50}$ compared to native virus in a constant cell line. Similarly, a "resistant virus" refers to a virus that exhibits a 2.5-fold, and more typically, five- or greater fold increase in $EC_{50}$ compared to naive virus in a constant cell line, including, but not limited to PBM, MT2 or MT4 cells. The term "resistance" is used in its most general sense and includes total resistance or partial resistance or decreased sensitivity to a nucleoside analogue.

The term "D-D4FC" is used herein interchangeably with the terms β-D-D4FC and DFC, below. The S68del mutation was selected in and confers resistance to DFC, and is expected to confer resistance to certain DFC prodrugs.

As used herein, the term "prodrug" refers to the 5' and $N^4$ acylated, alkylated, or phosphorylated (including mono, di, and triphosphate esters as well as stabilized phosphates and phospholipid) derivatives of D-D4FC. In one embodiment, the acyl group is a carboxylic acid ester in which the non-carbonyl moiety of the ester group is selected from straight, branched, or cyclic alkyl, alkoxyalkyl including methoxymethyl, aralkyl including benzyl, aryloxyalkyl including phenoxymethyl, aryl including phenyl optionally substituted by halogen, alkyl, alkyl or alkoxy, sulfonate esters such as alkyl or aralkyl sulphonyl including methanesulfonyl, trityl or monomethoxytrityl, substituted benzyl, trialkylsilyl, or diphenylmethylsilyl. Aryl groups in the esters optimally comprise a phenyl group. The alkyl group can be straight, branched or cyclic and is preferably $C_1$ to $C_{18}$.

As used herein, "S68del" refers to a novel deletion of sequences at codon 68 of HIV-RT, e.g., HIV-1 RT encoding sequences, which may alternatively be a deletion of the AGT codon 68 trinucleotide, or of the adjacent +1 frameshift trinucleotide GTA.

As used herein, "a codon 68 mutation" refers to a codon 68 substitution or S68del, but not a larger deletion that encompasses S68del.

The following terms, unless otherwise indicated, shall be understood to have the following meanings:

The term "allelic variant" refers to one of two or more alternative naturally-occurring forms of a gene, wherein each gene possesses a unique nucleotide sequence. In a preferred embodiment, different alleles of a given gene have similar or identical biological properties.

The term "polynucleotide" or "nucleic acid molecule" refers to a polymeric form of nucleotides of at least 10 bases in length. The term includes DNA molecules (e.g., cDNA or genomic or synthetic DNA) and RNA molecules (e.g., mRNA or synthetic RNA), as well as analogs of DNA or RNA containing non-natural nucleotide analogs, non-native internucleoside bonds, or both. The nucleic acid can be in any topological conformation. For instance, the nucleic acid can be single-stranded, double-stranded, triple-stranded, quadruplexed, partially double-stranded, branched, hairpinned, circular, or in a padlocked conformation. The term includes single and double stranded forms of DNA.

Unless otherwise indicated, a "nucleic acid comprising SEQ ID NO: X" refers to a nucleic acid, at least a portion of which has either (i) the sequence of SEQ ID NO: X, or (ii) a sequence complementary to SEQ ID NO: X. The choice between the two is dictated by the context. For instance, if the nucleic acid is used as a probe, the choice between the two is dictated by the requirement that the probe be complementary to the desired target.

An "isolated" or "substantially pure" nucleic acid or polynucleotide (e.g., an RNA, DNA or a mixed polymer) is one which is substantially separated from other cellular components that naturally accompany the native polynucleotide in its natural host cell, e.g., ribosomes, polymerases, and genomic sequences with which it is naturally associated. The term embraces a nucleic acid or polynucleotide that (1) has been removed from its naturally occurring environment, provided that it is not an unidentified member of a library which has not been separated from other members, (2) is not associated with all or a portion of a polynucleotide in which the "isolated polynucleotide" is found in nature, (3) is operatively linked to a polynucleotide which it is not linked to in nature, or (4) does not occur in nature. The term "isolated" or "substantially pure" also can be used in reference to recombinant or cloned DNA isolates, chemically synthesized polynucleotide analogs, or polynucleotide analogs that are biologically synthesized by heterologous systems.

However, "isolated" does not necessarily require that the nucleic acid or polynucleotide so described has itself been physically removed from its native environment. For instance, an endogenous nucleic acid sequence in the genome of an organism is deemed "isolated" herein if a heterologous sequence (i.e., a sequence that is not naturally adjacent to this endogenous nucleic acid sequence) is placed adjacent to the endogenous nucleic acid sequence, such that the expression of this endogenous nucleic acid sequence is altered. By way of example, a non-native promoter sequence can be substituted (e.g., by homologous recombination) for the native promoter of a gene in the genome of a human cell, such that this gene has an altered expression pattern. This gene would now become "isolated" because it is separated from at least some of the sequences that naturally flank it.

A nucleic acid is also considered "isolated" if it contains any modifications that do not naturally occur to the corresponding nucleic acid in a genome. For instance, an endogenous coding sequence is considered "isolated" if it contains an insertion, deletion or a point mutation introduced artificially, e.g., by human intervention. An "isolated nucleic acid" also includes a nucleic acid integrated into a host cell chromosome at a heterologous site, a nucleic acid construct present as an episome. Moreover, an "isolated nucleic acid" can be substantially free of other cellular material, or substantially free of culture medium when produced by recombinant techniques, or substantially free of chemical precursors or other chemicals when chemically synthesized.

As used herein, the phrase "degenerate variant" of a reference nucleic acid sequence encompasses nucleic acid sequences that can be translated, according to the standard genetic code, to provide an amino acid sequence identical to that translated from the reference nucleic acid sequence.

The term "percent sequence identity" or "identical" in the context of nucleic acid sequences refers to the residues in the two sequences which are the same when aligned for maximum correspondence. The length of sequence identity comparison may be over a stretch of at least about nine nucleotides, usually at least about 20 nucleotides, more usually at least about 24 nucleotides, typically at least about 28 nucleotides, more typically at least about 32 nucleotides, and preferably at least about 36 or more nucleotides. There are a number of different algorithms known in the art which can be used to measure nucleotide sequence identity. For instance, polynucleotide sequences can be compared using FASTA, Gap or Bestfit, which are programs in Wisconsin Package Version 10.0, Genetics Computer Group (GCG), Madison, Wis. FASTA provides alignments and percent sequence identity of the regions of the best overlap between the query and search sequences (Pearson, 1990). For instance, percent sequence identity between nucleic acid sequences can be determined using FASTA with its default parameters (a word size of 6 and the NOPAM factor for the scoring matrix) or using Gap with its default parameters as provided in GCG Version 6.1, herein incorporated by reference.

The term "substantial homology" or "substantial similarity," when referring to a nucleic acid or fragment thereof, indicates that, when optimally aligned with appropriate nucleotide insertions or deletions with another nucleic acid (or its complementary strand), there is nucleotide sequence identity in at least about 50%, more preferably 60% of the nucleotide bases, usually at least about 70%, more usually at least about 80%, preferably at least about 90%, and more preferably at least about 95%, 96%, 97%, 98%, 99%, 99.5% or 99.9% of the nucleotide bases, as measured by any well-known algorithm of sequence identity, such as FASTA, BLAST or Gap.

Alternatively, substantial homology or similarity exists when a nucleic acid or fragment thereof hybridizes to another nucleic acid, to a strand of another nucleic acid, or to the complementary strand thereof, under stringent hybridization conditions. "Stringent hybridization conditions" and "stringent wash conditions" in the context of nucleic acid hybridization experiments depend upon a number of different physical parameters. Nucleic acid hybridization will be affected by such conditions as salt concentration, temperature, solvents, the base composition of the hybridizing species, length of the complementary regions, and the number of nucleotide base mismatches between the hybridizing nucleic acids, as will be readily appreciated by those skilled in the art. One having ordinary skill in the art knows how to vary these parameters to achieve a particular stringency of hybridization.

In general, "stringent hybridization" is performed at about 25° C. below the thermal melting point (Tm) for the specific DNA hybrid under a particular set of conditions. "Stringent washing" is performed at temperatures about 5° C. lower than the Tm for the specific DNA hybrid under a particular set of conditions. The Tm is the temperature at which 50% of the target sequence hybridizes to a perfectly matched probe. See Sambrook et al., supra, page 9.51, hereby incorporated by reference. For purposes herein, "high stringency conditions" are defined for solution phase hybridization as aqueous hybridization (i.e., free of formamide) in 6×SSC (where 20×SSC contains 3.0 M NaCl and 0.3 M sodium citrate), 1% SDS at 65° C. for 8-12 hours, followed by two washes in 0.2×SSC, 0.1% SDS at 65° C. for 20 minutes. It will be appreciated by the skilled worker that hybridization at 65° C. will occur at different rates depending on a number of factors including the length and percent identity of the sequences which are hybridizing.

The nucleic acids (also referred to as polynucleotides) of this invention may include both sense and antisense strands of RNA, cDNA, genomic DNA, and synthetic forms and mixed polymers of the above. They may be modified chemically or biochemically or may contain non-natural or derivatized nucleotide bases, as will be readily appreciated by those of skill in the art. Such modifications include, for example, labels, methylation, substitution of one or more of the naturally occurring nucleotides with an analog, internucleotide modifications such as uncharged linkages (e.g., methyl phosphonates, phosphotriesters, phosphoramidates, carbamates, etc.), charged linkages (e.g., phosphorothioates, phosphorodithioates, etc.), pendent moieties (e.g., polypeptides), intercalators (e.g., acridine, psoralen, etc.), chelators, alkylators, and modified linkages (e.g., alpha anomeric nucleic acids, etc.) Also included are synthetic molecules that mimic polynucleotides in their ability to bind to a designated sequence via hydrogen bonding and other chemical interactions. Such molecules are known in the art and include, for example, those in which peptide linkages substitute for phosphate linkages in the backbone of the molecule.

The term "mutated" when applied to nucleic acid sequences means that nucleotides in a nucleic acid sequence may be inserted, deleted or changed compared to a reference nucleic acid sequence. A single alteration may be made at a locus (a point mutation) or multiple nucleotides may be inserted, deleted or changed at a single locus. In addition, one or more alterations may be made at any number of loci within a nucleic acid sequence. A nucleic acid sequence may be mutated by any method known in the art including but not limited to mutagenesis techniques such as "error-prone PCR" (a process for performing PCR under conditions where the copying fidelity of the DNA polymerase is low, such that a high rate of point mutations is obtained along the entire length of the PCR product. See, e.g., Leung, D. W., et al., Technique, 1, pp. 11-15 (1989) and Caldwell, R. C. & Joyce G. F., PCR Methods Applic., 2, pp. 28-33 (1992)); and "oligonucleotide-directed mutagenesis" (a process which enables the generation of site-specific mutations in any cloned DNA segment of interest. See, e.g., Reidhaar-Olson, J. F. & Sauer, R. T., et al., Science, 241, pp. 53-57 (1988)).

The term "vector" as used herein is intended to refer to a nucleic acid molecule capable of transporting another nucleic acid to which it has been linked. One type of vector is a "plasmid", which refers to a circular double stranded DNA loop into which additional DNA segments may be ligated. Other vectors include cosmids, bacterial artificial chromosomes (BAC) and yeast artificial chromosomes (YAC). Another type of vector is a viral vector, wherein additional DNA segments may be ligated into the viral genome (discussed in more detail below). Certain vectors are capable of autonomous replication in a host cell into which they are introduced (e.g., vectors having an origin of replication which functions in the host cell). Other vectors can be integrated into the genome of a host cell upon introduction into the host cell, and are thereby replicated along with the host genome. Moreover, certain preferred vectors are capable of directing the expression of genes to which they are operatively linked. Such vectors are referred to herein as "recombinant expression vectors" (or simply, "expression vectors").

"Operatively linked" expression control sequences refers to a linkage in which the expression control sequence is contiguous with the gene of interest to control the gene of interest, as well as expression control sequences that act in trans or at a distance to control the gene of interest.

The term "expression control sequence" as used herein refers to polynucleotide sequences which are necessary to affect the expression of coding sequences to which they are operatively linked. Expression control sequences are sequences which control the transcription, post-transcriptional events and translation of nucleic acid sequences. Expression control sequences include appropriate transcription initiation, termination, promoter and enhancer sequences; efficient RNA processing signals such as splicing and polyadenylation signals; sequences that stabilize cytoplasmic mRNA; sequences that enhance translation efficiency (e.g., ribosome binding sites); sequences that enhance protein stability; and when desired, sequences that enhance protein secretion. The nature of such control sequences differs depending upon the host organism; in prokaryotes, such control sequences generally include promoter, ribosomal binding site, and transcription termination sequence. The term "control sequences" is intended to include, at a minimum, all components whose presence is essential for expression, and can also include additional components whose presence is advantageous, for example, leader sequences and fusion partner sequences.

The term "recombinant host cell" (or simply "host cell"), as used herein, is intended to refer to a cell into which a recombinant vector has been introduced. It should be understood that such terms are intended to refer not only to the particular subject cell but to the progeny of such a cell. Because certain modifications may occur in succeeding generations due to either mutation or environmental influences, such progeny may not, in fact, be identical to the parent cell, but are still included within the scope of the term "host cell" as used herein. A recombinant host cell may be an isolated cell or cell line grown in culture or may be a cell which resides in a living tissue or organism.

The term "peptide" as used herein refers to a short polypeptide, e.g., one that is typically less than about 50 amino acids long and more typically less than about 30 amino acids long. The term as used herein encompasses analogs and mimetics that mimic structural and thus biological function.

Unless otherwise defined, all technical and scientific terms used herein have the same meaning as commonly understood by one of ordinary skill in the art to which this invention pertains. Exemplary methods and materials are described below, although methods and materials similar or equivalent to those described herein can also be used in the practice of the present invention and will be apparent to those of skill in the art. All publications and other references mentioned herein are incorporated by reference in their entirety. In case of conflict, the present specification, including definitions, will control. The materials, methods, and examples are illustrative only and not intended to be limiting.

S68del HIV-1 Mutant

In the present invention, the inventors have identified a mutant HIV-1 with a novel mutation in the HIV reverse transcriptase (RT) coding sequences. The novel mutation is a deletion in HIV-1 RT of the S68 codon ("S68del"). The S68del mutation was revealed during the selection of virus to dexelvucitabine (DFC) in primary human lymphocytes. The mutation reduces the sensitivity of HIV to nucleoside analogues to varying extents. The identification of this HIV-RT mutant and characterization of its phenotypic properties (e.g., its resistance and sensitivity profiles) are important for the development of assays to monitor NRTI treatment regimens and to screen for agents which can overcome the effects of the mutation.

HIV codon 68 mutants of the invention may be in isolated form such that they have undergone at least one purification step away from naturally occurring body fluids. Alternatively, the mutants may be maintained in isolated body fluid. In certain embodiments, the mutants may be in RNA or DNA form. The present invention also includes infectious molecular clones and nucleic acids comprising the genome or parts thereof from an HIV harboring a codon 68 mutation, such as, e.g., S68del.

It is possible that an HIV harboring a codon 68 mutation, such as, e.g., S68del, shows a greater relative fitness compared to wild-type HIV. Relative fitness can be measured by pairwise growth competition assays (Hu et al., *J. Acquir. Immune Defic. Syndr.* 2007; 45:494-500; Winters et al., *J. Virol.* 2000; 74; 10707-10713).

Nucleic Acids and Vectors, Viruses and Host Cells Comprising them

The invention provides a nucleic acid molecule comprising sequences encoding HIV-1 RT, and in some embodiments, encoding fragments of HIV-1 RT, the HIV-RT sequences comprising a codon 68 mutation. In certain embodiments, when the codon 68 mutation is an S68 substitution, it occurs alone or in combination with a mutation other than a K65R mutation. The invention also provides a nucleic acid molecule comprising sequences encoding part or all of HIV-1 RT, the HIV-RT sequences comprising a codon 68 mutation, wherein the codon 68 mutation is the only mutation in the HIV-RT sequences. The invention further provides a nucleic acid molecule comprising sequences encoding HIV-1 RT, the HIV-RT sequences comprising a codon 68 deletion wherein the S68 deletion removes the codon 68 AGT trinucleotide, or wherein the S68 deletion removes the GTA trinucleotide spanning codons 68 and 69. Preferably, isolated nucleic acid molecules of the invention comprise a minimum of nine, preferably of 10-25 or more nucleotides so that they may be used as selective primers, e.g., in nucleic acid amplification methods, or as probes in nucleic acid hybridization techniques.

The invention also provides vectors comprising any of the previously described nucleic acids. Such vectors may be RNA or DNA based, and may be replicative or integrative vectors, expression vectors (transient or stable), viral vectors and the like.

The invention also provides an isolated HIV, such as HIV-1 or HIV-2, comprising any of the previously described nucleic acids.

The invention also provides a host cell comprising any one of the nucleic acids or isolated HIV of the invention.

The present invention also provides HIV specific primers which may be used in conjunction with the methods and kits of the invention. In certain embodiments, a primer of the invention can be used to amplify a region of HIV-RT comprising codon 68 and preferably, can be used to distinguish between the presence and absence of an HIV reverse transcriptase codon 68 mutation, and more particularly, of the S68del mutation. Examples of such primers include, without limitation, SK38 Primer: ATA ATC CAC CTA TCC CAG TAG GAG AAA T (SEQ ID NO: 1) and SK39 Primer: TTT GGT CCT TGT CTT ATG TCC AGA ATG C (SEQ ID NO: 2). The presence of amplified product may also be detected with the SK19 probe: ATC CTG GGA TTA AAT AAA ATA GTA AGA ATG TAT AG (SEQ ID NO: 3). The invention thus also provides a nucleic acid probe that can be used to distinguish between the presence and absence of an HIV reverse transcriptase codon 68 mutation, and more particularly, of the S68del mutation. Other HIV specific primers and probes may easily be designed by those of skill in the art that can detect and differentiate codon 68 mutations, including those that distinguish between S68 substitutions and the codon 68 deletion referred to herein as "S68del".

Methods of Evaluating Effectiveness of an Antiretroviral Agent and of Monitoring the Progression of HIV-Infection The present invention provides methods for monitoring the clinical progression of human immunodeficiency virus (HIV) infection and its response to selected antiviral therapies. It involves, in certain embodiments, measuring HIV nucleic acid copy number in plasma or lymphocytes (e.g., peripheral blood mononuclear cells) derived from an HIV-infected person. Such measurements are performed, e.g., using RT (to copy RNA to cDNA where HIV RNA is being assessed) and quantitative real time polymerase chain reaction (PCR) assays, to assess an individual's HIV viral load. Direct measurement of viral loads enables one to evaluate the therapeutic effect of one or more select antiretroviral agents, and therapies comprising administering such agents. Genotypic analyses of HIV nucleic acid sequences and more specifically, of mutations that emerge during treatment with select antiretroviral agents allow one to understand how viral genotypic changes correlate with viral phenotypic characteristics and reveal how emerging mutations affect viral RNA levels in the presence of select antiretroviral agents. When a correlation between viral genotype and phenotypic characteristics is demonstrated, it provides useful methods that may be used, alone or in combination, for predicting clinical outcome and thus for improving patient management and care.

In working examples disclosed herein, a novel mutation of HIV RT (deletion of AGT at codon S68, "S68del") was selected in a dexelvucitabine (DFC)-treated primary human lymphocytes after 14 weeks of culture. The S68del mutation became the dominant virus by week 19 based on population sequence and clonal analysis. The S68del was investigated phenotypically against selected antiviral agents and cross resistance determined by drug susceptibility assays. The S68del correlated with refractoriness not only to DFC treatment (during which it emerged), but also to numerous other clinically important NSRI. Codon insertions and deletions have been associated with multi-drug resistance (MDR) in clinical samples from antiretroviral treated individuals (e.g., 76del, 69del, 69ins, 70del) but the S68del has never been reported.

Mutations at codon 68 of HIV-RT, and more particularly, of S68del, correlate with resistance to certain antiretroviral therapies, including DFC and lamivudine, emtricitabine, tenofovir, abacavir and amdoxovir monotherapies. Codon 68 mutants, and S68 del in particular, are expected to precede immunologic decline over time, e.g., by one or more, or 2-6 or more months. Once mutation such as a deletion at codon 68 has been detected in plasma HIV RNA or lymphocytes of an HIV-infected individual, a specific therapeutic regimen is considered. In cases in which the HIV-infected individual is already undergoing antiretroviral therapy, an alteration in the therapeutic regimen is preferably considered. For example, adding, subtracting or changing agents to overcome resistance to the treatment may be considered.

In certain embodiments of the invention, quantitative real-time PCR or other real-time sequence detection assays may be used to detect and monitor the absolute concentrations and relative proportions of virus with mutations at codon 68 (e.g., S68del) of HIV-RT, a mutation which correlates with resistance to therapy with DFC and cross-resistance to a number of other NRTI, including but not limited to lamivudine, emtricitabine, tenofovir, abacavir and amdoxovir. When mutation at codon 68 (e.g., S68del) has been detected in a person undergoing monotherapy with DFC or any other antiretroviral agent, an alteration in the therapeutic regimen is preferably considered for effective patient management. Such alteration may include, for example, combination therapy, e.g. adding AZT to the DFC or other antiretroviral agent under which the mutation is detected, or combination therapy with another antiviral agent that is effective in inhibiting viral replication of an HIV harboring the codon 68 mutation (e.g., S68del).

Accordingly, in one particular embodiment, the invention provides a method for evaluating the effectiveness to an HIV-infected individual of a selected antiretroviral agent or therapy, the method comprising: (i) collecting a sample from an HIV-infected person treated with an antiretroviral agent (the agent may be a antiretroviral compound or may be a composition comprising at least one antiretroviral compound); (ii) amplifying (e.g., by PCR) the HIV-encoding nucleic acid in the sample using HIV specific primers; and (iii) testing for the presence of HIV specific nucleic acid sequences in the amplification product of (ii). The sample from the HIV-infected individual may be derived, e.g., from plasma or lymphocytic cells, such as PMB cells, of the infected person. When the sample is plasma, the HIV encoded nucleic acid is predominantly viral RNA. When the sample is derived from lymphocytes, the HIV encoded nucleic acid is predominantly proviral DNA. In certain preferred embodiments, the HIV specific primers used in (ii) can distinguish between the presence and absence of a HIV reverse transcriptase codon 68 mutation, and more particularly, of the S68del mutation. In certain other separate embodiments, step (iii), and not necessarily step (ii), distinguishes between the presence and absence of a codon 68 mutation, e.g., S68del.

In a further embodiment, the invention provides a method for evaluating the effectiveness to an HIV-infected individual of a selected antiretroviral agent or therapy, the method comprising: (i) collecting a sample from an HIV-infected individual; and (ii) determining whether the sample comprises nucleic acid encoding HIV reverse transcriptase having a mutation at codon 68, e.g., S68del, in which the presence of the mutation correlates positively with refractoriness of the individual to the selected antiretroviral therapy and, if the therapy remains unchanged, to accelerated immunologic decline of the HIV-infected individual compared to HIV-infected individuals who do not have the mutation. The sample from the HIV-infected individual may be, e.g., plasma or lymphocytic cells such as PBM cells. When the sample is plasma, the HIV encoded nucleic acid is predominantly viral RNA. When the sample is lymphocytic cells, the HIV encoded nucleic acid is predominantly proviral DNA.

In any of the above methods, the absence of, or decreasing concentrations of, detectable HIV sequence correlates positively with the assessment that the antiretroviral agent is therapeutically effective in treating a codon 68, e.g., S68del, mutation. Moreover, in this method, the presence of, or increasing concentrations of, detectable HIV sequence correlates positively with the assessment that the antiretroviral agent is therapeutically ineffective.

In another embodiment, the invention provides methods for evaluating the effectiveness to an HIV-infected individual of treatment with a selected antiretroviral agent, comprising (i) collecting a sample from an HIV-infected individual before treatment with a selected antiretroviral agent; (ii) collecting a sample from the HIV-infected individual after treatment with the selected antiretroviral agent; (iii) amplifying separately HIV-encoding nucleic acid in the samples from (i) and (ii) with HIV primers; (iv) comparing the HIV nucleic acid copy number in samples (i) and (ii), wherein a ratio of HIV nucleic acid copy number in samples (i) and (ii) of greater than about 2.5 to 1, 4 to 1, 5 to 1, 10 to 1 or more, correlates positively with the assessment that the selected antiretroviral agent is therapeutically effective. The sample from the HIV-infected individual may be, e.g., plasma or lymphocytic cells such as PBM cells. When the sample is plasma, the HIV encoded nucleic acid is predominantly viral RNA. When the sample is lymphocytic cells, the HIV encoded nucleic acid is predominantly proviral DNA. In certain embodiments, such methods may additionally or optionally (e.g., in step (iii)) comprise the use of HIV primers that can distinguish between the presence and absence of a codon 68 mutation, e.g., S68del in HIV-RT.

Methods such as those described above may be modified to further include one or more steps of collecting and analyzing a sample from an HIV-infected individual so as to monitor the efficacy of the course of the individual's treatment over time and to make changes to the person's treatment regimen as needed, based on correlations derived from measuring and comparing HIV genomic mutations, and specific nucleic acid levels before and after treatment with a selected antiretroviral agent or therapy.

Accordingly, in certain embodiments, the invention provides methods for evaluating the effectiveness to an HIV-infected individual of treatment with a selected antiretroviral agent treatment prone to emergence of a codon 68 mutation, the method comprising: (i) collecting at least one sample from an HIV-infected individual at separate time intervals; (ii) amplifying HIV-encoding nucleic acid in the separate samples using HIV primers; (iii) measuring HIV nucleic acid copy numbers using the amplification products of step (ii); and (iv) comparing the HIV nucleic acid copy numbers in the samples collected during the course of the selected treatment; whereby a statistically significant decline in HIV nucleic acid copy numbers detected over the course of the treatment correlates positively with the assessment that the selected antiretroviral agent has not selected for a HIV-RT codon 68 mutation, e.g., S8del, and remains therapeutically effective. In certain embodiments, such methods may additionally or optionally (e.g., in step (iii)) comprise the use of HIV primers that can distinguish between the presence and absence of a codon 68 mutation, e.g., S68del in HIV-RT. The sample from the HIV-infected individual may be, e.g., plasma or lymphocytic cells such as PBM cells. When the sample is plasma, the HIV encoded nucleic acid is predominantly viral RNA. When the sample is lymphocytic cells, the HIV encoded nucleic acid is predominantly proviral DNA.

In other embodiments of the invention, the methods may be used to detect mutations at codon 68 of HIV-RT, e.g., S68del, which correlate with resistance to a selected antiretroviral therapy and which precede immunologic decline. Accordingly, the present invention provides methods for evaluating the effectiveness of a selected antiretroviral therapy to an HIV-infected individual, the method comprising: (i) collecting a sample from an HIV-infected individual who is being treated with an antiretroviral agent; and (ii) determining (for example, using quantitative, real time PCR) whether the sample comprises nucleic acid encoding HIV-RT having a mutation at codon 68, e.g., S68del, in which the presence of the mutation correlates positively with immunologic decline of the individual within at least one, two, three four, five, six or ten or more months. Under such circumstances, the HIV-infecting individual has become, via the mutation, resistant to the selected antiretroviral agent. It may be desirable after detecting the codon 68, e.g., S68del, mutation to alter the course of the person's current treatment regimen. The altered treatment regimen may be a complete exchange of antiretroviral compounds or agents or may comprise adding one or more additional antiretroviral agents to the HIV-infected individual's current treatment regimen. For example, if the individual was being treated with DFC when the mutation arose, the individual's therapeutic regimen may desirably be altered, within about a six to twelve month period of the mutation's occurrence, by either (i) changing to a different antiretroviral agent, such as zidovudine (AZT) and stopping DFC treatment; (ii) increasing the dosage of DFC (which is often less desirable); or (iii) adding another antiretroviral agent, such as zidovudine (AZT); to the person's therapeutic regimen; or any combination thereof. The effectiveness of the modification in therapy may be evaluated, as set forth above, by monitoring HIV nucleic acid copy numbers after the treatment change. A subsequent decrease in circulating HIV RNA copy number, for example, correlates positively with the effectiveness of the new treatment regimen.

Because the mutation at the codon 68, e.g., S68del, may appear first in plasma HIV RNA and only later in lymphocytic cell proviral DNA, monitoring the time course of appearance of the codon 68 mutation in proviral DNA may be desirable. Accordingly, the present invention also provides methods for evaluating the effectiveness to an HIV-infected person of antiretroviral therapy, the method comprising: (i) collecting lymphocytic cells from an HIV-infected person who is being treated with an antiretroviral agent; and (ii) determining whether the cells comprise proviral HIV DNA comprising a mutation at codon 68 (e.g., S68del), in which the presence of the mutation correlates positively with immunologic decline of the individual over time. (The time depends in part on how much sooner the mutation identified in the individual's plasma HIV RNA precedes the mutation being detected in proviral DNA, which may be anywhere from about 1 to about 5, 6, 7, 8, 9, 10 or more months). Detection of the codon 68, e.g., S68del, mutation in proviral DNA is an indicator of immunologic decline and alteration of the person's therapeutic regimen is desirable.

In a specific embodiment of the invention, a method for evaluating the effectiveness to an HIV-infected person of DFC therapy is provided, the method comprising: (i) collecting a sample (e.g., plasma) from an HIV-infected person who is being treated with DFC; (ii) amplifying the HIV-encoding RNA in the sample by converting the RNA to cDNA and amplifying HIV sequences using HIV primers and PCR, for example; and (iii) testing for the presence of HIV sequence in the amplification product of (ii), wherein the absence of detectable HIV sequence correlates positively with the conclusion that DFC is therapeutically effective and the presence of detectable HIV sequence correlates positively with the conclusion that DFC is therapeutically ineffective. In other embodiments, the sample from the HIV-infected individual is derived from or comprises lymphocytic cells and step (ii) comprises amplifying HIV proviral DNA sequences without a required conversion of RNA to cDNA. In preferred embodiments of the above methods, the HIV primers used comprise SK38 Primer: ATA ATC CAC CTA TCC CAG TAG GAG AAA T (SEQ ID NO: 1) and SK39 Primer: TTT GGT CCT TGT CTT ATG TCC AGA ATG C (SEQ ID NO: 2), and/or the presence of HIV sequence is detected using, e.g., an enzyme-linked assay (e.g., a colorimetric or fluorescence based assay). The presence of the amplified product may also be detected with the SK19 probe: ATC CTG GGA TTA AAT AAA ATA GTA AGA ATG TAT AG (SEQ ID NO: 3). Similar methods in which the HIV copy number is measured are also provided.

Another specific embodiment of the invention provides a method for evaluating the effectiveness to an HIV-infected individual of DFC therapy, the method comprising: (i) collecting a sample (e.g., plasma) from an HIV-infected individual who is being treated with DFC; (ii) amplifying the HIV-encoding RNA in the sample by converting the RNA to cDNA and amplifying HIV sequences using HIV primers and PCR to produce a PCR amplification product that comprises a portion of the HIV-RT gene containing codon 68 (e.g. SK38 Primer: ATA ATC CAC CTA TCC CAG TAG GAG AAA T (SEQ ID NO: 1) and SK39 Primer: TTT GGT CCT TGT CTT ATG TCC AGA ATG C (SEQ ID NO: 2)); and (iii) measuring the presence or absence of a mutation at codon 68 of the HIV-RT, wherein the presence of the mutation correlates positively with immunologic decline of the HIV-infected individual over time. In other embodiments, the sample from the HIV-infected individual is derived from or comprises lymphocytic cells and step (ii) comprises amplifying HIV proviral DNA sequences without a required conversion of RNA to cDNA. In preferred embodiments of the above methods, the HIV primers used comprise SK38 Primer: ATA ATC CAC CTA TCC CAG TAG GAG AAA T (SEQ ID NO: 1) and SK39 Primer: TTT GGT CCT TGT CTT ATG TCC AGA ATG C (SEQ ID NO: 2), and/or the presence of HIV sequence is detected using, e.g., an enzyme-linked assay (e.g., a colorimetric or fluorescence based assay). The presence of the amplified product may also be detected with the SK19 probe: ATC CTG GGA TTA AAT AAA ATA GTA AGA ATG TAT AG (SEQ ID NO: 3). Similar methods in which the HIV copy number is measured are also provided.

The presence of the codon 68, e.g., S68del, mutation indicates that the effectiveness of monotherapy with DFC is likely to decline either in the presence or the absence of the codon 68 mutation. Combination therapy with DFC (e.g., by adding AZT) or a switch to other drugs as provided herein is desirable.

Kits

The present invention also provides a kit for detection of mutations at codon 68 (e.g., S68del) of HIV-RT encoding sequences.

In certain embodiments, the kit comprises a first pair of PCR primers which bind outside the region of codon 68 and therefore may be used to amplify a DNA fragment comprising codon 68 (e.g. SK38 Primer: ATA ATC CAC CTA TCC CAG TAG GAG AAA T (SEQ ID NO: 1) and SK39 Primer: TTT GGT CCT TGT CTT ATG TCC AGA ATG C (SEQ ID NO: 2)); and at least two pairs of second round primers which may be used to amplify selectively codon 68, e.g., S68del, sequences. The kit may include more than two pairs of second primers. Similar primers may be readily designed by those skilled in the art; the first pair of primers need only amplify a conveniently-sized DNA fragment comprising codon 68 of HIV-RT, and one member of the second pair of primers should bind selectively to codon 68, preferably having its 3' terminus at the codon of interest in order to maximize the probability of a perfect match resulting in amplification. The kit may also include a probe for detection of the amplified product containing codon 68, such as the SK19 probe: ATC CTG GGA TTA AAT AAA ATA GTA AGA ATG TAT AG (SEQ ID NO: 3). Optionally, the kit may include instructions for interpretation indicting that the presence of the mutant form at the codon 68 of HIV-RT correlates with reduced efficacy of a particular antiretroviral therapeutic agent, e.g., that presence of the codon 68 mutant indicates reduced efficacy of monotherapy with DFC and a number of other NRTI, including but not necessarily limited to lamivudine, emtricitabine, tenofovir, abacavir and amdoxovir.

As shown herein, the S68del mutant HIV demonstrated greater than 30-fold increased resistance to DFC, lamivudine, emtricitabine, tenofovir, abacavir and amdoxovir. As expected, the S68del demonstrated no resistance to NNRTI and protease inhibitors. HIV-RT containing the S68 deletion demonstrated a 5.6-, 2.5- and 10-fold increase in resistance to DFC-TP, AZT-TP and emtricitabine-TP, respectively.

Viral Nucleic Acid and Protein Analyses

As detailed above, it is possible to study the quantity and/or quality (such as screening for mutations) of HIV-specific DNA or RNA sequences isolated from HIV-infected individuals (e.g., plasma samples or lymphocytic cells such as PBM cells) to evaluate whether a particular antiretroviral agent or therapy is an effective one. Well-known extraction and purification procedures are available for the isolation of DNA from a sample. Proviral DNA, for example, can be isolated from patient samples, such as from lymphocytic cells (e.g., PBM cells), by digestion of HIV-infected cells with proteinase K in the presence of EDTA and a detergent such as SDS, followed by extraction with phenol.

HIV-specific RNA can be isolated from samples such as plasma samples or lymphocytic cells, e.g., PBM cells, using the following methodology. Suitable infected cells are incubated for a period of time. The cells are recovered by centrifugation. The cells are resuspended in an RNA extraction buffer followed by digestion using a proteinase digestion buffer and digestion with proteinase K. Proteins are removed in the presence of a phenol/chloroform mixture. RNA can then be recovered following further centrifugation steps. (Maniatis, T., et al, *Molecular Coning, A Laboratory Manual*, 2nd Edition, Cold Spring Harbor Laboratory Press, (1989)).

Although it is possible to use non-amplified nucleic acid, due to the relative scarcity of nucleic acid in an HIV-1 sample, it is preferable to amplify it. Nucleic acid may be selectively amplified using the general technique of polymerase chain reaction (PCR), which is an in vitro method for producing large amounts of specific nucleic acid fragment of defined length and sequence from small amounts of a template.

A standard PCR comprises standard reactants, using $Mg^{2+}$ concentration, oligonucleotide primers and temperature cycling conditions for amplification of the HIV gene of interest, such as the HIV-RT gene, using sequence specific primers. The primers are chosen such that they will amplify the entire RT gene or a selected sequence which incorporates nucleotides corresponding to a region of the wild-type DNA sequence of HIV-1 that includes the codon which is mutated. In a preferred embodiment of the invention, primers 38K and 39K (SK38 Primer: ATA ATC CAC CTA TCC CAG TAG GAG AAA T (SEQ ID NO: 1) and SK39 Primer: TTT GGT CCT TGT CTT ATG TCC AGA ATG C (SEQ ID NO: 2)) are used to amplify the RT gene.

RNA cannot be amplified directly by PCR. Its corresponding cDNA must first be synthesized. Synthesis of cDNA is normally carried out by primed reverse transcription reactions using primers, such as for example, using oligo-dT primers which hybridize to polyA tails found at the 3'-end of many eukaryotic RNA transcripts (PolII). Advantageously, primers are chosen such that they will simplify the nucleic acid sequence for RT or a selected sequence which incorporates nucleotides corresponding to the region of RNA corresponding to the wild-type DNA sequence or to the region of the mutant DNA sequence corresponding to the 68th codon of the reverse transcriptase region. This could be achieved by preparing an oligonucleotide primer which is complementary to a region of the RNA strand which is upstream of the corresponding sequence of the wild-type DNA sequence. cDNA prepared by this methodology (see Maniatis, T., et al., supra.) can then be used in the same way as for the DNA already discussed.

The next stage of the methodology is to hybridize to the nucleic acid an oligonucleotide which is complementary to a region of the wild-type DNA sequence (or its corresponding RNA) or to a region of the mutant DNA sequence (or its corresponding RNA).

Conditions and reagents are then provided to permit polymerization of the nucleic acid from the 3'-end of the oligonucleotide primer. Such polymerization reactions are well-known in the art.

If the oligonucleotide primer has at its 3'-end a nucleotide which is complementary to a mutant genotype, that is a genotype which has a nucleotide change at the 68th codon in the RT region, then polymerization of the nucleic acid sequence will only occur if the nucleic acid of the sample is the same as the mutant genotype. Polymerization of a wild type nucleic acid sequence will not occur or at least not to a significant extent because of a mis-match of nucleotides at the 3'-end of the oligonucleotide primer and the nucleic acid sequence of the sample.

If the oligonucleotide primer has at its 3'-end of nucleotide which is complementary to the wild-type genotype, that is a genotype which has the wild-type nucleotide at the 68th codon in the RT region, then there will be polymerization of a nucleic acid sequence which is wild-type at that position. There will be no polymerization of a nucleic acid which has a mutant nucleotide at the 3'-position.

The preferred length of each oligonucleotide is 15-20 nucleotides, but may vary depending on selected hybridization conditions that are well known to the skilled worker. The oligonucleotide can be prepared according to methodology well known to the skilled worker (Koster, H., *Drug Research*, 30 p 548 (1980); Koster, H., *Tetrahedron Letters*, p 1527 (1972); Caruthers, *Tetrahedron Letters*, p 719, (1980); *Tetrahedron Letters*, p 1859, (1981); *Tetrahedron Letters* 24, p 245, (1983); Gate. M. *Nucleic Acid Research*, 8, p 1081, (1980)) and is generally prepared using an automated DNA synthesizer such as an Applied Biosystems 381A synthesizer.

It is convenient to determine the presence of an oligonucleotide primer extended product. The means for carrying out the detection is by using an appropriate label.

The label may be conveniently attached to the oligonucleotide primer or to some other molecule which will bind the primer extended polymerization product.

The label may be for example an enzyme, radioisotope or fluorochrome. A preferred label may be biotin which could be subsequently detected using streptavidin conjugated to an enzyme such as peroxidase or alkaline phosphatase. The presence of an oligonucleotide primer extended polymerization product can be detected for example by running the polymerization reaction on an agarose gel and observing a specific DNA fragment labeled with ethidium bromide, or Southern blotted and autoradiographed to detect the presence or absence of bands corresponding to polymerized product. If a predominant band is present which corresponds only to the labeled oligonucleotide then this indicates that polymerization has been occurred. If bands are present of the correct predicted size, this would indicate that polymerization has occurred.

For example, DNA isolated from HIV-infected individuals' plasma samples or PBM cells as described herein is used as a template for PCR amplification using synthetic oligonucleotide primers which either match or mis-match with the amplified sequences. The feasibility of PCR in detecting such mutations has already been demonstrated. PCR using the Amplification Refractory Mutation system ("ARMS") (Newton, C. R., et al. *Nucleic Acids Research*, 17, p 2503, (1989)) Synthetic oligonucleotide are produced that anneal to the regions adjacent to an including the specific mutations such that the 3'-end of the oligonucleotide either matches or mismatches with a mutant or wild-type sequence. PCR is carried out which results in the identification of a DNA fragment (using gel electrophoresis) where a match has occurred or no fragment where a mismatch occurred.

DNA is extracted from HIV-1 infected T-cells as described herein and subjected to "ARMS" PCR analysis using these primers.

The presence of a fragment is identified by using an oligonucleotide primer as described above, i.e., by attempting polymerization using an oligonucleotide primer which may be labeled for the amplified DNA fragment under stringent conditions which only allow hybridization of complementary DNA (the only difference is that differential hybridization does not have to be performed as fragments of DNA amplified by the "ARMS" method will be the same whether derived from mutant or wild-type DNS, so a common oligonucleotide can be used to detect the presence of these fragments. The sequence of such an oligonucleotide is derived from a DNA sequence within the DNA fragment that is conserved amongst HIV-1 strains).

The above PCR assay may be adapted to enable direct detection of mutations associated with D-D4FC resistance in DNA from PBL samples from infected individuals that have not been cultured to obtain virus. As this material generally contains considerably less HIV-1 DNA than that in infected lymphoid cultures a "double PCR" (or nested set) protocol can be used (Simmonds et al., *J. Virol.*, 64, 864-872, (1990)) to boost the amount of target HIV-1 RT DNA signal in the samples. The double PCR overcomes the problem of limited amplification of a rare template sequence. A small amount of the pre-amplified material may be used in the second PCR with primer pairs designed to allow discrimination of wild type and mutant residues.

The presence of a codon 68 mutation in RT can also be determined by quantitative real-time PCR, as described in Example 4.

It is also possible to detect codon 68 mutations in the HIV-1 RT RNA isolated from clinical samples using an RNA amplification system. Using the methodology described by Guatelli et al. (*Proc. Natl. Acad. Sci*, (*USA*), 8/7, 1874-1878, (March 1990)) a target nucleic acid sequence can be replicated (amplified) exponentially in vitro under isothermal conditions by using three enzymatic activities essential to retroviral replication: reverse transcriptase, RNase H and a DNA-dependant RNA polymerase. Such a methodology may be employed followed by an hybridization step to distinguish mutant from wild-type nucleotides at discussed previously.

The viral RNA or corresponding DNA from an HIV-infected person may be directly assayed. Alternatively, part or all of the HIV-RT encoding sequences may be cloned into viral vectors and amplified to produce larger amounts of viral nucleic acid for sequencing and other desired analyses.

According to this aspect of the invention, detection may be any nucleic acid-based detection means, for example nucleic acid hybridization techniques or polymerase chain reaction (PCR). The invention further encompasses the use of different assay formats of said nucleic acid-based detection means, including restriction fragment length polymorphism (RFLP), amplified fragment length polymorphism (AFLP), single-strand chain polymorphism (SSCP), amplification and mismatch detection (AMD), interspersed repetitive sequence polymerase chain reaction (IRS-PCR), inverse polymerase chain reaction (iPCR) and reverse transcription polymerase chain reaction (RT-PCR), among others.

Suitable assay means also include nucleic acid hybridization protocols such as Northern blots and Southern blots.

In certain embodiments of the invention, the presence of the S68del mutation may be detected by solid-state nucleic acid sensors. In specific embodiments, the solid-state sensors are oligonucleotide microarrays, cDNA microarrays and nucleic acids bound to any other convenient solid supports, such as beads or other microspheres. Examples of such sensors are further described in Sievertzon et al., *Expert Rev. Mol. Diagn.* 2006; 6:481-492; Heller, *Annu. Rev. Biomed. Eng.* 2002; 4:129-153; and Watson et al., *Curr. Opinion in Biotech.* 1998; 9:609-614.

In one specific embodiment, a line probe assay can be used to detect the codon 68, e.g., S68del, mutation in samples collected from HIV-infected individuals. Oligonucleotide probes used to detect the S68del mutation, for example, are applied to a nitrocellulose or other suitable membrane. RNA or DNA isolated from HIV-infected individuals is amplified and labeled, for example, by biotinylation. The labeled nucleic acid is reverse hybridized to the probes, and the amount of hybridized nucleic acid is detected. Details of probe itemization, nitrocellulose strip production and reverse hybridization have been published previously (Stuyver et al., *J. Clin. Microbiol.* 1996; 34:2259-2266; Stuyver et al., *Antimicrob. Agents Chemother.* 1997; 41:284-291; Van Geyt et al., in *Therapies of Viral Hepatitis* 1998; 139-145).

Any of a number of available systems and assays may be used in conjunction with products and methods of the invention to assess viral genotypes and associated phenotypes such as antiretroviral drug susceptibility, including but not limited to certain commercially available systems (see, e.g., PhotoSense™ HIV (Monogram Biosciences); HIV GenoSure™ (LabCorp; see also Baxter et al., AIDS 2000 14(9):F83-93 (2000) and Durant et al., Lancet 353(9171): 2195-2199 (1999); Antivirogram® (Virco) and Kellam, *Antimicrob. Agents Chemother.* 38:23-30 (1994)).

In other embodiments, the S68del mutation sequence and drug resistance profile may be added to HIV genotyping and phenotyping databases. Samples isolated from an HIV-infected individual may then be compared to such databases to correlate the viral genotype and/or viral phenotype of the individual sample to effective antiretroviral therapies. In particular, such methods comprising comparison to information stored in a database may be used to choose effective NRTI treatment (including NRTI in combination with one or more other NRTI and/or other agents) (see, e.g., Lengauer et al., *Nature Rev. Microbiol.* 4:790-797 (2006); Baxter et al., *AIDS* 2000 14:F83-F93 (2000); and Durant et al., *Lancet* 353(9171):2195-2199 (1999)).

Alternatively, the HIV RT protein may be screened directly or indirectly for the mutation using any of a number of available protein sequence based techniques. Such techniques include protein expression based assays, optionally in combination with Western blotting techniques. In certain embodiments, a denatured form of the HIV RT protein containing the S68del mutation may be used to raise antibodies that bind differentially to denatured S68del and the wild-type RT proteins (or fragments thereof comprising the S68 codon). A variety of protein expression systems are known and available to the skilled worker. The RT may be expressed in a baculovirus system, for example. Antibodies having specificity for an S68del specific epitope that may be engineered include monoclonal, chimeric, humanized or human antibodies, and also include any number of antibody fragments and single chain antibodies. The antibody that binds the S68del and the wild-type forms of RT differentially can be used in Western blots, ELISAs and other immunoassays to detect the presence of the S68del HIV mutation in samples from HIV-infected individuals.

Methods to Avoid Selecting, or to Treat an Individual Harboring, HIV with a Codon 68 Mutation in HIV-RT The invention further provides methods for treating a subject infected with HIV-1 or HIV-2 comprising the step of administering over time an antiretroviral agent that does not select for an HIV-1 mutant having a codon 68 mutation in the HIV reverse transcriptase coding sequence.

In one embodiment, the antiretroviral agent administered to avoid selecting HIV-1 with a codon 68 mutation is a protease inhibitor. Examples of protease inhibitors include, but are not limited to, lopinavir, indinavir (Crixivan), nelfinavir ([3S-[2(2S*,3S*),3-alpha,4-a-beta,8a-beta-]]-N-(1,1-dimethylethyl)decahydro-2-)2-hydroxy-3-[(3-hydroxy-2-methylbenzoyl)amino]-4-(phenylthio)butyl]-3-isoquinolinecarboxamide mono-methanesulfonate) (Viracept), saquinavir (Invirase), or 141W94 (amprenavir; (S)-tetrahydrofuran-3-yl-N-[(1S,2R)-3-[N-[(4-aminophenyl)sulfonyl]-N-isob-utylamino]-1-benzyl-2-hydroxypropyl]carbamate, efavirenz (S)-6-chloro4-(cyclopropylethynyl)-1,4-dihydro4-(trifluoromethyl)-2H-3,1-benzoxazin-2-one.), atazanavir sulfate (Reyataz) and Darunavir (Prezista).

In another embodiment, the antiretroviral agent administered to avoid selecting HIV-1 with a codon 68 mutation is an NNRTI. Examples of NNRTI include, but are not limited to, DMP-266 ((S)-6-chloro-4-cyclopropylethynyl-4-trifluoromethyl-1,4-dihydro-2H-3,1-b-enzoxazin-2-one (SUSTIVA, see U.S. Pat. No. 5,519,021); delavirdine, (1-[3-(1-methyl-ethyl)amino]-2-pyridinyl-4-[[5-[(methylsulfonyl) amino]-1H-indol-2-yl]carbonyl]-, monoethanesulfonate), nevirapine, or delavirdine.

In other embodiments, HIV-infected individuals can be treated with NRTI against which the S68del mutant does not show increased resistance. Examples of such NRTI include AZT, DDI, DFDOC, D4T, DOT and DDC.

In other embodiments, the antiretroviral agent administered to avoid selecting HIV-1 with a codon 68 mutation is an HIV fusion inhibitor, an HIV integrase inhibitor, an RNAse H inhibitor, a CD4 binding inhibitor, a CXCR4 binding inhibitor, or a CCR5 binding inhibitor.

The present invention further provides methods for isolating compounds that are active against an HIV-1 S68del mutant using the screening methods and the S68del mutant HIV of the invention. A variety of protocols for characterizing antiretroviral agents and their effects on viral replication, in vitro and in vivo, such as those described and exemplified herein, are well known in the literature. See, e.g., Lennerstrand et al., *Antimicrob. Agents Chemother.* 2007 Apr. 2 (Epub ahead of print); Hammond et al., *Antimicrob. Agents Chemother.* 49(9):3930-3932 (2005); Moser et al., *Antimicrob. Agents Chemother.* 49(8):3334-3340 (2005); Parikh et al., *Antimicrob. Agents Chemother.* 49(3): 1139-1144 (2005); Boyer et al., *J. Virol.* 78(18):9987-9997 (2004); Roge et al., *Antiviral Therapy* 8:173-182 (2003); Boyer et al., *J. Virol.* 76(18):9143-9151 (2002); Van Vaerenbergh, *Verh. K. Acad. Geneeskd. Belg.* 63(5):447-473 (2001); Tamalet et al., *Virol.* 270:310-316 (2000); and Bazmi et al., *Antimicrob. Agents Chemother.* 44(7):1783-1788 (2000); each incorporated herein by reference. These or similar methods may be used to characterize known antiretroviral compounds and to identify and isolate new antiretroviral compounds that are useful in the treatment of multidrug resistant HIV-1, such as the HIV-1 S68del mutant of the invention.

The dosages for such antiretroviral agents will depend on such factors as absorption, biodistribution, metabolism and excretion rates for each drug as well as other factors known to those of skill in the art. It is to be noted that dosage values will also vary with the severity of the condition to be alleviated. It is to be further understood that for any particular subject, specific dosage regimens and schedules should be adjusted over time according to the individual need and the professional judgment of the person administering or supervising the administration of the compositions. Examples of suitable dosage ranges for anti-HIV compounds, including nucleoside derivatives or protease inhibitors can be found in the scientific literature and in the Physicians Desk Reference. Many examples of suitable dosage ranges for other compounds described herein are also found in public literature or can be identified using known procedures. These dosage ranges can be modified as desired to achieve a desired result.

Preparation of Pharmaceutical Compositions

Any antiretroviral agent described herein can be administered to the HIV-infected individual as a pharmaceutically acceptable salt or prodrug in the presence of a pharmaceutically acceptable carrier or diluent, for any of the indications or modes of administration as described in detail herein. The active materials can be administered by any appropriate route, for example, orally, parenterally, enterally, intravenously, intradermally, subcutaneously, transdermally, intranasally or topically, in liquid or solid form.

The active compound(s) are included in the pharmaceutically acceptable carrier or diluent in an amount sufficient to deliver to a HIV-infected individual a therapeutically effective amount of compound to inhibit viral replication in vivo, especially HIV replication, without causing serious toxic effects in the treated individual. By "inhibitory amount" is meant an amount of active ingredient sufficient to exert an inhibitory effect on viral replication as measured by, for example, an assay such as the ones described herein. Preferably, inhibitory effect is at least 2.5-fold, and preferably at least 4-fold, 5-fold, 7-fold, 10-fold or higher.

A preferred dose of the compound for all the above-mentioned conditions will be in the range from about 1 to 75 mg/kg, preferably 1 to 20 mg/kg, of body weight per day, more generally 0.1 to about 100 mg per kilogram body weight of the recipient per day. The effective dosage range of the pharmaceutically acceptable derivatives can be calculated based on the weight of the parent nucleoside to be delivered. If the derivative exhibits activity in itself, the effective dosage can be estimated as above using the weight of the derivative, or by other means known to those skilled in the art.

The compounds are conveniently administered in unit any suitable dosage form, including but not limited to one containing 7 to 3000 mg, preferably 70 to 1400 mg of active ingredient per unit dosage form. An oral dosage of 50 to 1000 mg is usually convenient.

Ideally, the active ingredient should be administered to achieve peak plasma concentrations of the active compound of from about 0.02 to 70 micromolar, preferably about 0.5 to 10 mM. This may be achieved, for example, by the intravenous injection of a 0.1 to 25% solution of the active ingredient, optionally in saline, or administered as a bolus of the active ingredient.

The concentration of active compound in the drug composition will depend on absorption, distribution, metabolism and excretion rates of the drug as well as other factors known to those of skill in the art. It is to be noted that dosage values will also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed composition. The active ingredient may be administered at once, or may be divided into a number of smaller doses to be administered at varying intervals of time.

A preferred mode of administration of the active compound is oral. Oral compositions will generally include an inert diluent or an edible carrier. They may be enclosed in gelatin capsules or compressed into tablets. For the purpose of oral therapeutic administration, the active compound can be incorporated with excipients and used in the form of tablets, troches, or capsules. Pharmaceutically compatible bind agents, and/or adjuvant materials can be included as part of the composition.

The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring. When the dosage unit form is a capsule, it can contain, in addition to material of the above type, a liquid carrier such as a fatty oil. In addition, dosage unit forms can contain various other materials which modify the physical form of the dosage unit, for example, coatings of sugar, shellac, or other enteric agents.

The compounds can be administered as a component of an elixir, suspension, syrup, wafer, chewing gum or the like. A syrup may contain, in addition to the active compounds, sucrose as a sweetening agent and certain preservatives, dyes and colorings and flavors.

The compounds or their pharmaceutically acceptable derivative or salts thereof can also be mixed with other active materials that do not impair the desired action, or with materials that supplement the desired action, such as antibiotics, antifungals, antiinflammatories, protease inhibitors, or other nucleoside or non-nucleoside antiviral agents, as discussed in more detail above. Solutions or suspensions used for parental, intradermal, subcutaneous, or topical application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parental preparation can be enclosed in ampoules, disposable syringes or multiple dose vials made of glass or plastic.

If administered intravenously, preferred carriers are physiological saline or phosphate buffered saline (PBS).

Liposomal suspensions (including liposomes targeted to infected cells with monoclonal antibodies to viral antigens) are also preferred as pharmaceutically acceptable carriers these may be prepared according to methods known to those skilled in the art, for example, as described in U.S. Pat. No. 4,522,811 (which is incorporated herein by reference in its entirety). For example, liposome formulations may be prepared by dissolving appropriate lipid(s) (such as stearoyl phosphatidyl ethanolamine, stearoyl phosphatidyl choline, arachadoyl phosphatidyl choline, and cholesterol) in an inorganic solvent that is then evaporated, leaving behind a thin film of dried lipid on the surface of the container. An aqueous solution of the active compound or its monophosphate, diphosphate, and/or triphosphate derivatives is then introduced into the container. The container is then swirled by hand to free lipid material from the sides of the container and to disperse lipid aggregates, thereby forming the liposomal suspension.

Controlled Release Formulations

Any antiretroviral agent described herein can be administered as a controlled release formulation. The field of biodegradable polymers has developed rapidly since the synthesis and biodegradability of polylactic acid was reported by Kulkarni et al., in 1966 (*Arch. Surg.*, 93:839). Examples of other polymers which have been reported as useful as a matrix material for delivery devices include polyanhydrides, polyesters such as polyglycolides and polylactide-co-glycolides, polyamino acids such as polylysine, polymers and copolymers of polyethylene oxide, acrylic terminated polyethylene oxide, polyamides, polyurethanes, polyorthoesters, polyacrylonitriles, and polyphosphazenes. See, for example, U.S. Pat. Nos. 4,891,225 and 4,906,474 (polyanhydrides), U.S. Pat. No. 4,767,628 (polylactide, polylactide-co-glycolide acid), and U.S. Pat. No. 4,530,840, et al. (polylactide, polyglycolide, and copolymers). See also U.S. Pat. No. 5,626,863 which describes photopolymerizable biodegradable hydrogels as tissue contacting materials and controlled release carriers (hydrogels of polymerized and crosslinked macromers comprising hydrophilic oligomers having biodegradable monomeric or oligomeric extensions, which are end capped monomers or oligomers capable of polymerization and crosslinking); and PCT WO 97/05185 directed to multiblock biodegradable hydrogels for use as controlled release agents for drug delivery and tissue treatment agents.

Degradable materials of biological origin are well known, for example, crosslinked gelatin. Hyaluronic acid has been crosslinked and used as a degradable swelling polymer for biomedical applications (U.S. Pat. No. 4,957,744).

Many dispersion systems are currently in use as, or being explored for use as, carriers of substances, particularly biologically active compounds. Dispersion systems used for pharmaceutical and cosmetic formulations can be categorized as either suspensions or emulsions. Suspensions are defined as solid particles ranging in size from a few manometers up to hundreds of microns, dispersed in a liquid medium using suspending agents. Solid particles include microspheres, microcapsules, and nanospheres. Emulsions are defined as dispersions of one liquid in another, stabilized by an interfacial film of emulsifiers such as surfactants and lipids. Emulsion formulations include water in oil and oil in water emulsions, multiple emulsions, microemulsions, microdroplets, and liposomes. Microdroplets are unilamellar phospholipid vesicles that consist of a spherical lipid layer with an oil phase inside, as defined in U.S. Pat. Nos. 4,622,219 and 4,725,442. Liposomes are phospholipid vesicles prepared by mixing water-insoluble polar lipids with an aqueous solution. The unfavorable entropy caused by mixing the insoluble lipid in the water produces a highly ordered assembly of concentric closed membranes of phospholipid with entrapped aqueous solution.

U.S. Pat. No. 4,938,763 discloses a method for forming an implant in situ by dissolving a nonreactive, water insoluble thermoplastic polymer in a biocompatible, water soluble solvent to form a liquid, placing the liquid within the body, and allowing the solvent to dissipate to produce a solid implant. The polymer solution can be placed in the body via syringe. The implant can assume the shape of its surrounding cavity. In an alternative embodiment, the implant is formed from reactive, liquid oligomeric polymers which contain no solvent and which cure in place to form solids, usually with the addition of a curing catalyst.

A number of patents disclose drug delivery systems that can be used to administer D-D4FC or a nucleotide or other defined prodrug thereof. U.S. Pat. No. 5,749,847 discloses a method for the delivery of nucleotides into organisms by electroporation. U.S. Pat. No. 5,718,921 discloses microspheres comprising polymer and drug dispersed therewithin. U.S. Pat. No. 5,629,009 discloses a delivery system for the controlled release of bioactive factors. U.S. Pat. No. 5,578,325 discloses nanoparticles and microparticles of non-linear hydrophilic hydrophobic multiblock copolymers. U.S. Pat. No. 5,545,409 discloses a delivery system for the controlled release of bioactive factors. U.S. Pat. No. 5,494,682 discloses ionically cross-linked polymeric microcapsules.

U.S. Pat. No. 5,728,402 describes a controlled release formulation that includes an internal phase which comprises the active drug, its salt or prodrug, in admixture with a hydrogel forming agent, and an external phase which comprises a coating which resists dissolution in the stomach. U.S. Pat. Nos. 5,736,159 and 5,558,879 discloses a controlled release formulation for drugs with little water solubility in which a passageway is formed in situ. U.S. Pat. No. 5,567,441 discloses a once-a-day controlled release formulation. U.S. Pat. No. 5,508,040 discloses a multiparticulate pulsatile drug delivery system. U.S. Pat. No. 5,472,708 discloses a pulsatile particle based drug delivery system. U.S. Pat. No. 5,458,888 describes a controlled release tablet formulation which can be made using a blend having an internal drug containing phase and an external phase which comprises a polyethylene glycol polymer which has a weight average molecular weight of from 3,000 to 10,000. U.S. Pat. No. 5,419,917 discloses methods for the modification of the rate of release of a drug form a hydrogel which is based on the use of an effective amount of a pharmaceutically acceptable ionizable compound that is capable of providing a substantially zero-order release rate of drug from the hydrogel. U.S. Pat. No. 5,458,888 discloses a controlled release tablet formulation.

U.S. Pat. No. 5,641,745 discloses a controlled release pharmaceutical formulation which comprises the active drug in a biodegradable polymer to form microspheres or nanospheres. The biodegradable polymer is suitably poly-D,L-lactide or a blend of poly-D,L-lactide and poly-D,L-lactide-co-glycolide. U.S. Pat. No. 5,616,345 describes a controlled absorption formulation for once a day administration that includes the active compound in association with an organic acid, and a multi-layer membrane surrounding the core and containing a major proportion of a pharmaceutically acceptable film-forming, water insoluble synthetic polymer and a minor proportion of a pharmaceutically acceptable film-forming water soluble synthetic polymer. U.S. Pat. No. 5,641,515 discloses a controlled release formulation based on biodegradable nanoparticles. U.S. Pat. No. 5,637,320 discloses a controlled absorption formulation for once a day administration. U.S. Pat. Nos. 5,580,580 and 5,540,938 are directed to formulations and their use in the treatment of neurological diseases. U.S. Pat. No. 5,533,995 is directed to a passive transdermal device with controlled drug delivery. U.S. Pat. No. 5,505,962 describes a controlled release pharmaceutical formulation.

Prodrug Formulations

Any of antiretroviral agents which are described herein can be administered as an acylated prodrug or a nucleotide prodrug, as described in detail below.

Any of the nucleosides described herein or other compounds that contain a hydroxyl or amine function can be administered as a nucleotide prodrug to increase the activity, bioavailability, stability or otherwise alter the properties of the nucleoside. A number of nucleotide prodrug ligands are known. In general, alkylation, acylation or other lipophilic modification of the hydroxyl group of the compound or of the mono, di or triphosphate of the nucleoside will increase the stability of the nucleotide. Examples of substituent groups that can replace one or more hydrogens on the phosphate moiety or hydroxyl are alkyl, aryl, steroids, carbohydrates, including sugars, 1,2-diacylglycerol and alcohols. Many are described in R. Jones and N. Bischofberger, Antiviral Research, 27 (1995) 1-17. Any of these can be used in combination with the disclosed nucleosides or other compounds to achieve a desired effect.

The active nucleoside or other hydroxyl containing compound can also be provided as an ether lipid (and particularly a 5'-ether lipid for a nucleoside), as disclosed in the following references, which are incorporated by reference herein: Kucera et al., 1990, AIDS Res. Hum. Retro Viruses. 6:491-501; Piantadosi et al., 1991, *J. Med. Chem.* 34:1408.1414; Hosteller et al., 1992, *Antimicrob. Agents Chemother.* 36:2025.2029; Hostetler et al., 1990, *J. Biol. Chem.* 265: 61127.

Non-limiting examples of U.S. patents that disclose suitable lipophilic substituents that can be covalently incorporated into the nucleoside or other hydroxyl or amine containing compound, preferably at the 5'-OH position of the nucleoside or lipophilic preparations, include U.S. Pat. Nos. 5,149,794; 5,194,654 5,223,263; 5,256,641; 5,411,947; 5,463,092; 5,543,389; 5,543,390; 5,543,391; and 5,554,728, each of which is incorporated herein by reference. Foreign patent applications that disclose lipophilic substituents that can be attached to the nucleosides of the present invention, or lipophilic preparations, include WO 89/02733, WO 90/00555, WO 91/16920, WO 91/18914, WO 93/00910, WO 94/26273, WO 96/15132, EP 0 350 287, EP 93917054.4, and WO 91/19721.

Non-limiting examples of nucleotide prodrugs are described in the following references: Ho, D. H. W. (1973) *Cancer Res.* 33, 2816-2820; Holy, A. (1993) In: De Clercq (Ed.), Advances in Antiviral Drug Design, Vol. I, JAI Press, pp. 179-231; Hong et al. (1979a) *Biochem. Biophys. Res. Commun.* 88, 1223-1229; Hong et al. (1980) *J. Med. Chem.* 28, 171-177; Hosteller et al. *J. Biol. Chem.* 265, 6112-6117; Hosteller et al. (1991) *J. Biol. Chem.* 266, 11714-11717; Hosteller et al. (1994a) *Antiviral Res.* 24, 59-67; Hosteller et al. (1994b) *Antimicrobial Agents Chemother.* 38, 2792-2797; Hunston et al. (1984) *J. Med. Chem.* 27, 440-444; Ji et al. (1990) *J. Med. Chem.* 33 2264-2270; Jones et al. (1984) *J. Chem. Soc. Perkin Trans. I,* 1471-1474; Juodka, B. A. and Smart, J. (1974) Coll. Czech. Chem. Comm. 39, 363-968; Kataoka et al. (1989) *Nucleic Acids Res. Sym. Ser.* 21, 1-2; Kataoka, S., and Uchida *Heterocycles* 32, 1351-1356; Kinchington et al. (1992) *Antiviral Chem. Chemother.* 3, 107-112; Kodama et al. (1989) *Jpn. J. Cancer Res.* 80, 679-685; Korty, M. and Engels, J. (1979) *Naunyn-Schmiedeberg's Arch. Pharmacol.* 310, 103-111; Kumar et al. (1990) *J. Med. Chem.,* 33, 2368-2375; LeBec, C., and Huynh-Dinh, T. (1991) *Tetrahedron Lett.* 32, 6553-6556; Lichtenstein et al. (1960) *J. Biol. Chem.* 235, 457-465; Lucthy et al. (1981) *Mitt. Geg. Lebensmittelunters. Hyg.* 72, 131-133 (Chem. Abstr. 95, 127093); McGigan, et al. (1989) *Nucleic Acids Res.* 17, 6065-6075; McGuigan et al. (1990a) 3'-*Antiviral Chem. Chemother.* 1 107-113; McGuigan et al. (1990b) *Antiviral Chem. Chemother.* 1, 355-360; McGuigan et al. (1990c) *Antiviral Chem. Chemother.* 1, 25-33; McGuigan et al. (1991) *Antiviral Res.* 15, 255-263; McGuigan et al. (1993b) *J. Med. Chem.* 36, 1048-1052.

Alkyl hydrogen phosphate derivatives of the anti-HIV agent AZT may be less toxic than the parent nucleoside analogue. *Antiviral Chem. Chemother.* 5, 271-277; Meyer et al. (1973) *Tetrahedron Lett.* 269-272; Nagyvary et al. (1973) *Biochem. Biophys. Res. Commun.* 55, 1072-1077; Namane et al. (1992) *J. Med. Chem.* 35, 3039-3044; Nargeot et al. (1983) *Proc. Natl. Acad. Sci. U.S.A.* 80, 2395-2399; Nelson et al. (1987) *J. Am. Chem. Soc.* 109, 4058-4064; Nerbonne et al. (1984) *Nature* 301, 74-76; Neumann et al. (1989) *J. Am. Chem. Soc.* 111, 4270-4277; Ohno et al. (1991) *Oncology* 48, 451-455; Palomino et al. (1989) *J. Med. Chem.* 32, 22-625; Perkins et al. (1993) *Antiviral Res.* 20 (Suppl. I). 84; Piantadosi et al. (1991) *J. Med. Chem.* 34, 1408-1414; Pompon et al. (1994). *Antiviral Chem. Chemother.* 5, 91-98; Postemark, T. (1974) *Annu. Rev. Pharmacol.* 14, 23-33; Prisbe et al. (1986) *J. Med. Chem.* 29, 671-675; Pucch et al. (1993) *Antiviral Res.* 22, 155-174; Pugaeva et al. (1969) *Gig. Trf Prof. Zabol.* 14, 47-48 (Chem. Abstr. 72, 212); Robins, R. K. (1984) *Pharm. Res.* 11-18; Rosowsky et al. (1982) *J. Med. Chem.* 25, 171-178; Ross, W. (1961) *Biochem. Pharm.* 8, 235-240; Ryu et al. (1982) *J. Med. Chem.* 25, 1322-1329; Saffhill et al. (1986) *Chem. Biol. Interact.* 57, 347-355; Saneyoshi et al. (1980) *Chem. Pharm. Bull.* 28, 2915-2923; Sastry et al. (1992) *Mol. Pharmacol.* 41, 441-445; Shaw et al. (1994) 9th Annual AAPS Meeting. San Diego, Calif. (Abstract); Shuto et al. (1987) *Tetrahedron Lett.* 28, 199-202; Shuto et al. (1988) *Pharm. Bull* 36, 209-217. An example of a useful phosphate prodrug group is the S-acyl-2-thioethyl group, also referred to as "SATE".

Standard reference works setting forth the general principles of recombinant DNA technology known to those of skill in the art include Ausubel et al., CURRENT PROTOCOLS IN MOLECULAR BIOLOGY, John Wiley & Sons, New York (1998 and Supplements to 2001); Sambrook et al., MOLECULAR CLONING: A LABORATORY MANUAL, 2d Ed., Cold Spring Harbor Laboratory Press, Plainview, N.Y. (1989); Kaufman et al., Eds., HANDBOOK OF MOLECULAR AND CELLULAR METHODS IN BIOLOGY AND MEDICINE, CRC Press, Boca Raton (1995); McPherson, Ed., DIRECTED MUTAGENESIS: A PRACTICAL APPROACH, IRL Press, Oxford (1991). Standard reference works setting forth the general principles of retrovirology known to those of skill in the art include RETROVIRUSES, Coffin, John M.; Hughes, Stephen H.; Varmus, Harold E., Plainview (NY): Cold Spring Harbor Laboratory Press (1997) and ANTIRETROVIRAL RESISTANCE IN CLINICAL PRACTICE, Gerretti, Anna Maria, editor London: Mediscript Ltd. (2006). Standard reference works setting forth the general principles of immunology known to those of skill in the art include: Harlow and Lane ANTIBODIES: A LABORATORY MANUAL, 2d Ed., Cold Spring Harbor Laboratory Press, Cold Spring Harbor, N.Y. (1999); and Roitt et al., IMMUNOLOGY, 3d Ed., Mosby-Year Book Europe Limited, London (1993). Standard reference works setting forth the general principles of medical physiology and pharmacology known to those of skill in the art include: Harrison's PRINCIPLES OF INTERNAL MEDICINE, 14th Ed., (Anthony S. Fauci et al., editors), McGraw-Hill Companies, Inc., 1998.

All publications and patents cited are hereby incorporated by reference in their entirety.

Throughout this specification and paragraphs, the word "comprise" or variations such as "comprises" or "comprising" will be understood to imply the inclusion of a stated integer or group of integers but not the exclusion of any other integer or group of integers.

The following are examples which illustrate the compositions and methods of this invention. These examples should not be construed as limiting: the examples are included for the purposes of illustration only. This invention has been described with reference to its preferred embodiments. Variations and modifications of the invention, will be obvious to those skilled in the art from the foregoing detailed description of the invention. It is intended that all of these variations and modifications be included within the scope of this invention.

EXAMPLES

Example 1

Discovery of S68del Virus in DFC-Treated Viral Pool

Compound.

β-D-2',3'-didehydro-2',3'-dideoxy-5-fluorocytidine (DFC, D-d4FC, RVT).

Cells.

Peripheral blood mononuclear (PBM) cells were separated by ficoll-hypaque (Histopaque 1077: Sigma) density gradient centrifugation from Buffy coats obtained from the American Red Cross (Atlanta, Ga.). Buffy coats were derived from healthy seronegative donors. Cells were activated with 3 µg/ml phytohaemagglutinin A (Sigma-Aldrich, St. Louis, Mo.) in 500 ml of RPMI-1640 (Mediatech Inc., Herndon, Va.) containing 100 ml heat-inactivated fetal bovine serum (Hyclone), 83.3 IU/ml penicillin, 83.3 µg/ml streptomycin, 1.6 mM L-glutamine (Mediatech Inc., Herndon, Va.), for 2-3 days prior to use.

Virus.

HIV-1/LAI obtained from the Centers for Disease Control and Prevention (Atlanta, Ga.) was used as the virus for the resistant pool. A multiplicity of infection (MOI) of 0.1, as determined by a limiting dilution method in PBM cells, was selected to begin the infected pool.

Selection of Resistant Virus.

Naive PBM cells were treated with DFC at 0.1 µM for one hour prior to inoculation with HIV-1/LAI. The treated PBM cell group and a control nontreated PBM cell group were allowed to infect for 1 hr. IL-2 (26 IU/ml)-supplemented RPMI-1640 was then added for a final concentration of $1 \times 10^6$ cells/ml. Virus was passaged every 6 days with a fresh treatment of DFC, ranging from 0.1 µM to 6 µM over 52 weeks. RT activity was measured weekly and used to determine percent inhibition of DFC. Total RNA was isolated from culture supernatants using the commercial QIAmp Viral RNA mini kit (Qiagen, Valencia, Calif.). Reverse transcriptase PCR was performed using Invitrogen Superscript Reverse Transcriptase III to generate second strand cDNA from viral RNA using Ambion DECAprime II primers. PCR was performed using Invitrogen Platinum Taq polymerase (high fidelity). A 1346 bp fragment of the HIV-1 genome was amplified using forward primer 5'-ttgactcagat-tggttgcactttaa-3' (SEQ ID NO: 4) and reverse primer 5'-aagaacccatagtaggagcagaaac-3' (SEQ ID NO: 5). The PCR product was purified using the QIAquick PCR purification kit. The samples were sequenced in both directions for the HIV-1 RT amino acids 01-300. Sequencing was performed in parallel between the control virus and DFC treated virus to determine if there were any mutations created by the applied drug pressure on weeks when the virus appeared to be resistant (Table 1 (WT—wild type); FIG. 1).

Population sequencing of virus during this assay revealed a disruption of the S68 codon in the reverse transcriptase (RT) sequence, which may alternatively be a deletion of the AGT codon 68 trinucleotide, or of the adjacent +1 frameshift trinucleotide GTA (Table 2).

TABLE 2

Amino acid sequence changes for S68del mutation.

| Mutation | HIV-$1_{LAI}$ sequence | Sequence Change |
|---|---|---|
| S68del | 67/GAC 68/AGT 69/ACT (SEQ ID NO: 6) | 67/GAC 69/ACT 70/AAA (SEQ ID NO: 7) |

The S68del mutation was first detected by population sequencing at week 14 as a mix with wild-type (WT) (Table 1). By week 19, S68del dominated the pool. At week 25, some K65R was detected as well. In week 28, only K65R was detectable. At week 52, the pool contained a mixture of S68del and K65R.

Cloning of the S68del virus demonstrated that S68del can occur independently or as a mixture with wild-type, K65R, T69A or T69S. Sometimes the mutations can be found in the same genome. No other mutation in the reverse transcriptase region was detected.

Deletions that occur in the RT region between codons 67 and 69 have been known to occur in combination with T69G or Q151M mutations (Hu et al., *J. Acquir. Immune Defic. Syndr.* 2007; 45:494-500; Winters et al., *J. Virol.* 2000; 74; 10707-10713). The alignment of published sequences with the S68del sequence as seen in Table 3 shows that the S68 deletion occurred without any associated mutations in the β3-β4 loop. The published sequences were found in clinical samples from patients that had undergone multiple drug treatments for HIV-1 infection and occurred with other

TABLE 1

Selection of S68del HIV-1 in DFC-treated human PBM cells.

| DFC (µM) | Culture week | Mutation by population sequencing | Number of clones sequenced S68Δ | K65R | WT | Total | Percentages of isolates containing RT mutations |
|---|---|---|---|---|---|---|---|
| 0 | 4 | WT | | | | | |
| 0.1 | 10 | WT | | | | | |
| 1 | 11 | WT | | | 10 | 10 | 100% WT |
| 1 | 12 | WT | | | | | 100% WT |
| 0.1 | 14 | S68Δ/WT | 5 | | 1 | 7 | 72% S68Δ, 14% WT, 14% S68N |
| 0.1 | 15 | WT | | | | | |
| 0.1 | 16 | WT | 3 | | 8 | 11 | 27% S68Δ, 73% WT |
| 1 | 17 | S68Δ/WT | 2 | | 5 | 7 | 29% S68Δ, 71% WT |
| 1 | 18 | S68Δ/WT | 2 | | 2 | 4 | 50% S68Δ, 50% WT |
| 1 | 19 | S68Δ | | | 7 | 7 | 100% WT |
| 0 | 20 | S68Δ | 12 | 1 | 1 | 14 | 86% S68Δ, 7% K65R, 7% WT |
| 1 | 22 | S68Δ | | | | | |
| 0 | 23 | S68Δ | 28 | | | 29 | 94% S68Δ, 6% S68Δ + T69 or T69S |
| 2 | 24 | S68Δ | | | | | |
| 3 | 25 | S68Δ/K65R/WT | | | | | |
| 3 | 26 | S68Δ/K65R/WT | 2 | 8 | | 10 | 20% S68Δ, 80% K65R |
| 3 | 27 | S68Δ/K65R/WT | 1 | 7 | | 8 | 12% S68Δ, 88% K65R |
| 6 | 28 | K65R | | | | | |
| 6 | 29 | K65R | | 8 | | 8 | 100% K65R |
| 6 | 30 | K65R | | 8 | | 8 | 100% K65R |
| 1.5 | 36 | K65R | | | | | |
| 6 | 49 | K65R | | | | | SN negative |
| 6 | 52 | S68Δ/K65R | 5 | 2 | 1 | 8 | 63% S68Δ + K65R, 25% K65R, 12% WT | multiple drug resistant (MDR) mutations (Table 3; AF271766: Boyer et al., *J. Virol.* 2004; 78:9987-97; AF311203: Hammond et al., *Antimicrob. Agents Chemother.* 2005; 49:3930-2; DQ394304: Hu et al., *J. Acquir. Immune Defic. Syndr.* 2007; 45:494-500; AF311157: Tamalet et al., *Virology* 2000; 270:310-6; and EF154395: Villena et al., *Journal of Virology* 2007, 81:4713-4721). In contrast, the S68del mutation was discovered in vitro in PBM cells under monotherapy.

TABLE 3

Alignment of the S68del sequence with previously published HIV-1 RT deletions.

| Virus | Deletion | RT region of HIV-1 | | | | | | | | | | |
|---|---|---|---|---|---|---|---|---|---|---|---|---|
| | | 63 | 64 | 65 | 66 | 67 | 68 | 69 | 70 | 71 | 72 | 73 |
| S68deletion | S68Δ | I | K | K | K | D | – | T | K | W | R | K (SEQ ID NO: 12) |
| AF271766 | D67Δ, T69G, K70R | I | K | K | K | – | S | G | R | W | R | K (SEQ ID NO: 13) |
| AF311203 | K70Δ, S68N | I | K | K | K | D | N | T | – | W | R | K (SEQ ID NO: 14) |
| DQ394304 | K70Δ, S68G | I | K | K | K | D | G | T | – | W | R | K (SEQ ID NO: 15) |
| AF311157 | T69Δ, D67S, S68G | I | K | K | K | S | G | – | K | W | R | K (SEQ ID NO: 16) |
| EF154395 | T69Δ, S68G, K70G | I | K | K | K | D | G | – | G | W | R | K (SEQ ID NO: 17) |
| LAI | | I | K | K | K | D | S | T | K | W | R | K (SEQ ID NO: 18) |
| pNL4-3 | | I | K | K | K | D | S | T | K | W | R | K (SEQ ID NO: 19) |

Mutated sequences are in bold and large font.

Example 2

Drug Susceptibility of In Vitro-Selected S68del HIV-1

Mutations that occur in the HIV-1 RT region between amino acids 62 and 78 increase NRTI resistance significantly (Hu et al., *J. Acquir. Immune Defic. Syndr.* 2007; 45:494-500). Drug resistance of the S68del virus isolated at week 23 ($HIV_{s68\Delta\text{-}23}$) was measured with the 3H-TTP RT incorporation assay in human PBM cells (Schinazi, et al., *Antimicrob. Agents Chemother.* 1990; 34:1061-1067; Stuyver et al., *Antimicrob. Agents Chemother.* 2002; 46:3854-60). $HIV_{s68\Delta\text{-}23}$ was population sequenced to ensure the dominant population was the deletion at codon 68. TOPO® cloning (Invitrogen) performed on $HIV_{s68\Delta\text{-}23}$ indicated that approximately 90% of the population was pure S68del. The other approximately 10% either had a T69 deletion or S68del with a mutation T69A. The susceptibility of the S68del virus to several nucleoside reverse transcriptase inhibitors (NRTI), a non-nucleoside reverse transcriptase inhibitor (NNRTI) and a protease inhibitor (PI) was tested. Fold increases were measured relative to $HIV_{LAI}$ (Table 4, FIGS. 2 and 3). Data are the averages of 2-6 independent experiments.

TABLE 4

Drug susceptibility results for $HIV_{s68\Delta\text{-}23}$.

| Virus | Compound | EC50 (μM) | EC90 (μM) | FI EC50 (μM) | FI EC90 (μM) |
|---|---|---|---|---|---|
| S68Δ-23 | AZT | 0.0038 | 0.0140 | 1.4 | 0.7 |
| | DOT | 0.66 | 3.47 | 3.7 | 3.3 |
| | Sustiva | 0.00039 | 0.0035 | 3.8 | 1.6 |
| | Lopinavir | 0.006 | 0.019 | 0.49 | 0.59 |
| | Abacavir | 3.9 | 11.3 | 47.3 | 8.7 |
| | D4T | 0.41 | 1.5 | 4.1 | 4.8 |
| | DDI | 0.63 | 4.5 | 1.2 | 2.5 |
| | DDC | 0.22 | 0.93 | 2.5 | 3.4 |
| | DFDOC | 0.44 | 1.45 | 4.8 | 4.2 |
| | DFC | 1.1 | 3.4 | 34.4 | 9.2 |
| | DAPD | 7.9 | 34.5 | 38.2 | 32.4 |
| | 3TC | 0.88 | 3.3 | 43.5 | 31.7 |
| | (–)-FTC | 0.30 | 1.1 | 62.5 | 48.1 |
| | TDF | 0.43 | 1.6 | 33.7 | 5.3 |
| | DXG | 1.6 | 5.1 | 6.2 | 3.7 |

Figure 2:
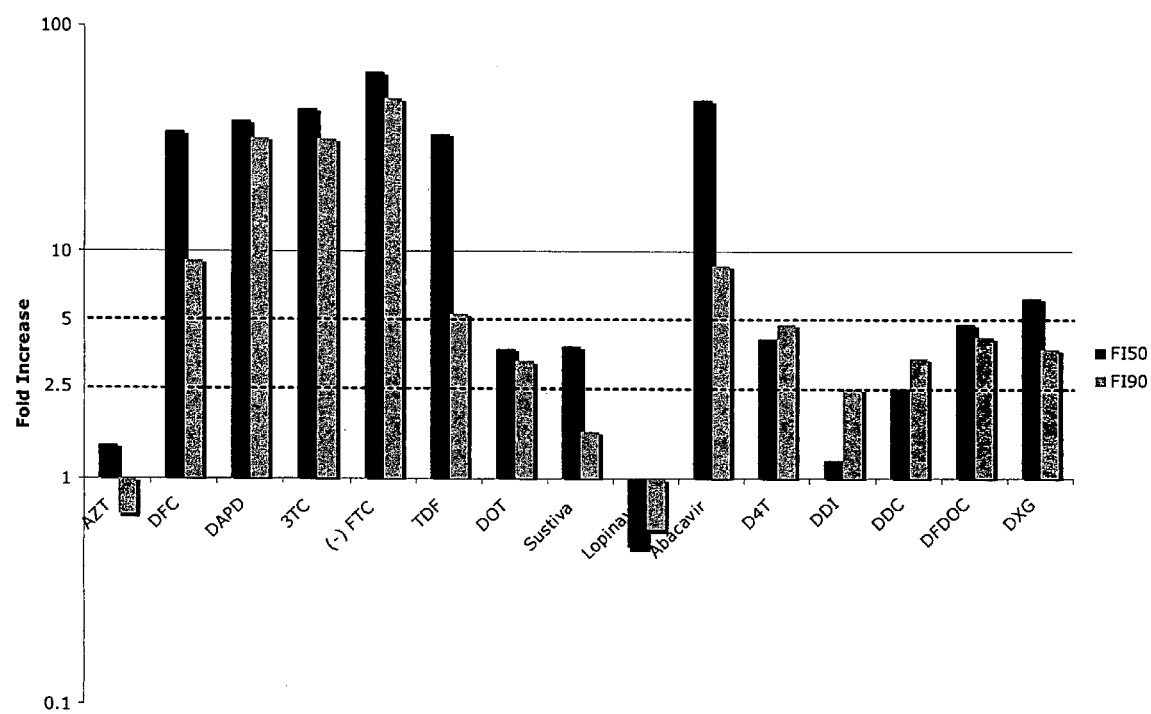
FIG. 2 is a graph showing the results of drug inhibition of the S68del virus. Inhibition was measured using the $^3$H-TTP RT incorporation assay. Fold increases were calculated relative to $HIV_{LAI}$. FI50—fold increase in 50% effective concentration. FI90—fold increase in 90% effective concentration. AZT—3'-azido3'-deoxythymidine; DFC—dexelvu- citabine; DAPD—(-)-beta-D-2,6-diaminopurine dioxolane; 3TC—lamivudine; (-) FTC—emtricitabine; TDF—tenofovir disoproxil fumarate; DOT—1-(beta-D-dioxolane)thymine; D4T—stavudine; DDI—didanosine; DDC—zalcitabine; D-FDOC—2',3'-dideoxy-5-fluoro-oxycytidine; DXG—(-)-9-(beta-D-dioxolane)guanine.
Figure 3:
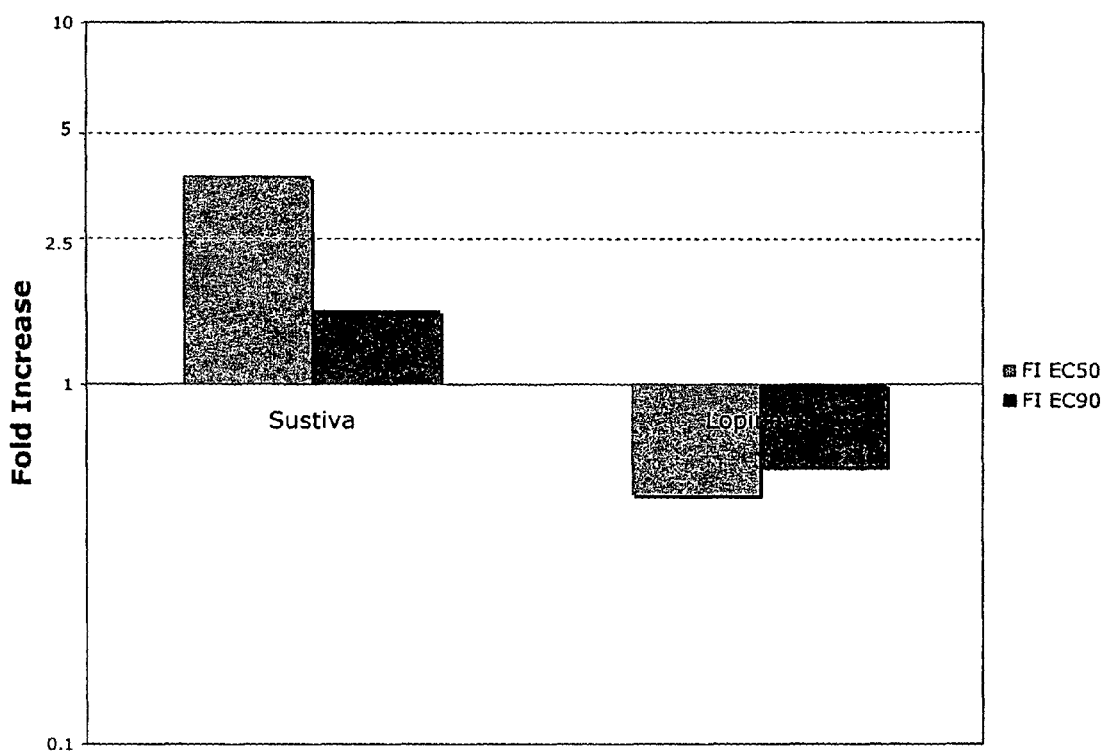
FIG. 3 is a graph showing the results of non-nucleoside reverse transcriptase inhibitor (Sustiva®) and protease inhibitor (Lopinavir®) inhibition of the S68del virus. Inhibition was measured using the $^3$H-TTP RT incorporation assay. Fold increases were calculated relative to $HIV_{LAI}$. FI $EC_{50}$—fold increase in 50% effective concentration. FI $EC_{90}$—fold increase in 90% effective concentration.
Figure 4:
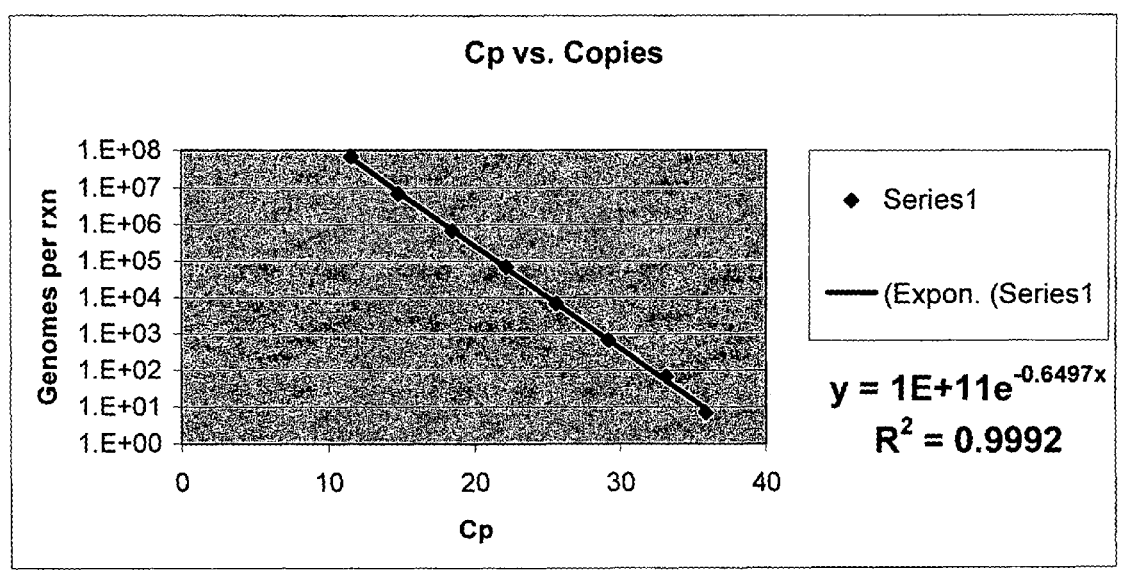
FIG. 4 is a graph generated by the HIV-1 Real-Time PCR assay for quantifying S68del virus levels in human peripheral blood mononuclear (PBM) cells. Cp—cycle number of crossing point.

Drug abbreviations are defined in the description of FIG. 2. FI $EC_{50}$ - fold increase in 50% effective concentration. FI $EC_{90}$ - fold increase in 90% effective concentration.

$HIV_{s68\Delta\text{-}23}$ showed increased resistance (FI $EC_{50}$ greater than 5) against NRTI such as DFC, DXG, DAPD, TDF, 3TC, abacavir and (–)FTC. $HIV_{s68\Delta\text{-}23}$ showed modest resistance (FI $EC_{50}$ between 2.5 and 5) against NRTI such as D-FDOC, D4T, DDC, and DOT. $HIV_{s68\Delta\text{-}23}$ showed no resistance (FI $EC_{50}$ less than 2.5) against NRTI such as DDI and AZT. $HIV_{s68\Delta\text{-}23}$ susceptibility to NNRTI (Sustiva®) or PI (Lopinavir®) was not significantly changed.

Example 3

Construction of S68del HIV-1 by Site-Directed Mutagenesis

An S68del mutant HIV-1 was reconstructed by site-directed mutagenesis using the Stratagene Quick II XL Site Directed Mutagenesis Methodology (Stratagene). An intermediate vector with a 4 kb fragment of pNL4-3 (AF3244930) containing the RT coding region was cloned into the pCR2.1 vector (Invitrogen). Primers MC0014F: CAA TAC TCC AGT ATT TGC CAT AAA GAA AAA AGA CAC TAA ATG GAG AAA ATT AGT AGA TTT CAG AGA AC (SEQ ID NO: 8) and MC0015R: GTT CTC TGA AAT CTA CTA ATT TTC TCC ATT TAG TGT CTT TTT TCT TTA TGG CAA ATA CTG GAG TAT TG (SEQ ID NO: 9) were selected according to Stratagene strategy. Using these primers, the S68del mutation was generated in the intermediate vector and confirmed by sequencing. The HIV-1 fragment from the intermediate vector was digested with Spe I/Age I and subcloned into the full-length pNL4-3 vector. The S68del pNL4-3-based infectious clone was then transfected into HEK293T cells and supernatant was collected after 4 days. The supernatant obtained from HEK293T was used to infect fresh PBM cells, after which the HIV-1 virus pool was passaged to establish an infective pool.

Example 4

Site-Directed Mutagenesis for Protein Expression

A site directed S68 deletion mutant was created by digesting pCR 2.1 (Invitrogen) and pNL4-3 (AF3244930) with restriction enzymes Eco RI and Spe I. The pCR2.1 was cut into a single band of 3.9 kb, and the pNL4-3 was cut into one 4.2 kb band and one 10.6 kb band. Nucleic acids were separated by gel electrophoresis in a TAE gel and extracted from bands using the Qiagen gel extraction kit. The 4.2 kb band from pNL4-3 containing the HIV-RT encoding sequences was ligated into the linearized pCR2.1, making the construct MC002. Site directed mutagenesis was performed on the MC002 plasmid. Primers used had the S68 codon AGT deleted, thus introducing the S68 deletion into the pNL4-3 RT background. Presence of the S68 codon AGT deletion (and no other surrounding mutations) was confirmed by sequencing in both directions.

To ligate the RT of pNL4-3 comprising the deletion at S68 codon 68 into protein expression vector pE60 (Invitrogen), MC002 was amplified using forward primer 5'-CGCGC-CCATGGYGCCCATTAGTCCTATTGAGACTGTACC-3' (SEQ ID NO: 10) and reverse primer 5'-GCGCGCA-GATCTTAGTACTTTCCTGATTCC AGCACTGAC-3' (SEQ ID NO: 11). The PCR product and pQE60 were digested with Bgl II and Nco I. The digested products were separated by gel electrophoresis nucleic acids in excised gel bands extracted using the Qiagen gel extraction kit. The amplified PCR product comprising the RT of pNL4-3 was ligated into the linearized pQE60. The ligation mix was transformed into chemically competent bacteria (Alpha-select). Plasmid DNA from selected transformants was extracted using a mini-prep kit (Qiagen). Plasmid DNA was sequenced in both directions to confirm the ligation.

Example 5

Quantitative HIV-1 Real-Time PCR Assay for Determining Viral Load of S68del HIV-1

The real-time PCR assay for quantifying virus levels in PBM cells serves as a more sensitive method for measuring drug resistance of S68del HIV-1 than other standard methods. Results for this assay performed for pNL4-3 are shown in FIG. 4. SK38 Primer: ATA ATC CAC CTA TCC CAG TAG GAG AAA T (SEQ ID NO: 1) and SK39 Primer: TTT GGT CCT TGT CTT ATG TCC AGA ATG C (SEQ ID NO: 2) were used in the real-time PCR assay. The presence of amplified product was detected with the SK19 probe: ATC CTG GGA TTA AAT AAA ATA GTA AGA ATG TAT AG (SEQ ID NO: 3). The resistance of S68del virus in the pNL4-3 background ($S68del_{pNL4-3}$) against AZT and DFC was measured by this assay (Table 5). Four concentrations were tested in duplicate for each data point.

TABLE 5

Resistance of $S68del_{pNL4-3}$ against AZT and DFC in human PBM cells measured by quantitative real-time PCR.

| Samples | pNL4-3 μM | S68del in pNL4-3 | Fold Increase for S68del | |
|---|---|---|---|---|
| AZT EC50 = | 0.13 | 0.10 | AZT FI50 = | 0.73 |
| EC90 = | 0.33 | 0.30 | AZT FI90 = | 0.89 |
| DFC EC50 = | 0.21 | 3.1 | DFC FI50 = | 14.7 |
| EC90 = | 2.3 | 8.5 | DFC FI90 = | 3.7 |

Drug abbreviations are defined in the description of FIG. 2. $EC_{50}$ -50% effective concentration. $EC_{90}$ - 90% effective concentration. FI50 - fold increase in 50% effective concentration. FI90 - fold increase in 90% effective concentration.

$S68del_{pNL4-3}$ showed increased resistance against DFC, but not against AZT. These results confirmed results obtained by the $^3$H-TTP RT incorporation assay and the heteropolymeric-DNA colorimetric RT assay with the in vitro selected S68del virus. Thus, the results show that the $S68del_{pNL4-3}$ virus will be a useful and valid construct to measure S68del drug resistance phenotypes. Furthermore, the real-time PCR assay will serve as an accurate method for measuring drug resistance. Finally, these results confirm that the deletion of the AGT codon 68 trinucleotide, or deletion of the adjacent +1 frameshift trinucleotide GTA, is solely responsible for increased resistance of the virus to growth in the presence of DFC.

Example 6

Enzymatic Characterization of the Recombinant S68del Reverse Transcriptase by a Heteropolymeric DNA Polymerase Assay The principle and performance of the non-radioactive RT assay has been described (Lennerstrand et al., *Antimicrob. Agents Chemother.* 2007; 51:2078-2084). Separate kit components, such as covalently-linked DNA microtiter plates and tracer solution (alkaline phosphate (AP)-conjugated anti-BrdU antibody) were obtained from Cavidi Tech, Uppsala, Sweden. In brief, the 96-well microtiter plate used consisted of an 18 base heteropolymeric DNA primer covalently bound to the well. In the RT assay, the DNA primer is bound to a 50-base DNA template at 50 ng/well (190 nM) with a 5'-$A_{12}$-3' tail with a 5'-$(GTCA)_5$-3' repeat (Integrated DNA Technologies, USA). The RT assay reaction mixture (total volume 150 μl/well) contained: Hepes 50 mM, pH 7.3; $MgCl_2$ 10 mM; Triton X-100 0.5%; bovine serum albumin 0.1 mg/ml; dATP, dGTP, dCTP and 5-bromo-2'-deoxyuridine-5'-triphosphate (BrdUTP) at 1.0 μM each (where BrdUTP replaces TTP) (Sigma). To obtain ATP primer unblocking reaction in the assay, the ATP (Amersham/GE Health Care) was set to physiological concentration (3.2 mM). However, the ATP was only used in the assay with virus pellets as sample, not merely for primer unblocking reaction but to protect degradation of substrate in the crude sample. Furthermore, the dNTP level including BrdUTP was increased from 1 μM to 4 μM for the assay with the virus pellet samples. Subsequently, in the assay with recombinant purified RT enzyme, no ATP besides 1 μM dNTP was used.

The reaction was started with the addition of RT either as recombinant or crude virus pellet form in a similar activity range as previous published (Lennerstrand et al., *Antimicrob. Agents Chemother.* 2007; 51:2078-2084). The RT reaction mixture was incubated at 33° C. for 180 min and terminated by NaOH (to dehybridize the template) and water washing of the plates. The tracer incubation step with anti-BrdU antibodies-AP-conjugated and the detection step for color absorbance at 405 nm was performed as previously described (Lennerstrand et al., *Antimicrob. Agents Chemother.* 2007; 51:2078-2084. The NRTI-TP used were AZT-TP (Cavidi Tech), DFC-TP and (−) FTC-TP. The latter nucleotides were synthesized from the corresponding nucleoside analog (Ludwig et al., *J. Org. Chem.* 1989; 54:631-635).

Figure 5:
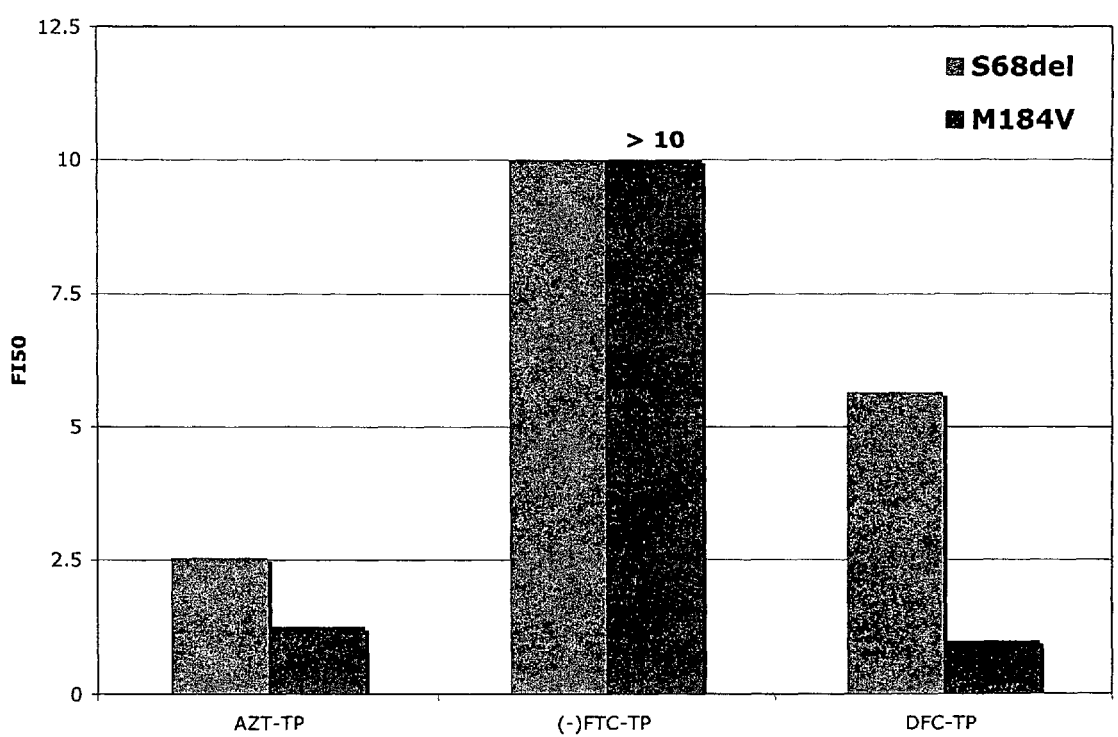
FIG. 5 is a graph showing the results of a heteropolymeric DNA colorimetric RT assay performed with particle-derived S68del and M184V RTs. FI50—fold increase in 50% effective concentration.
Figure 6:
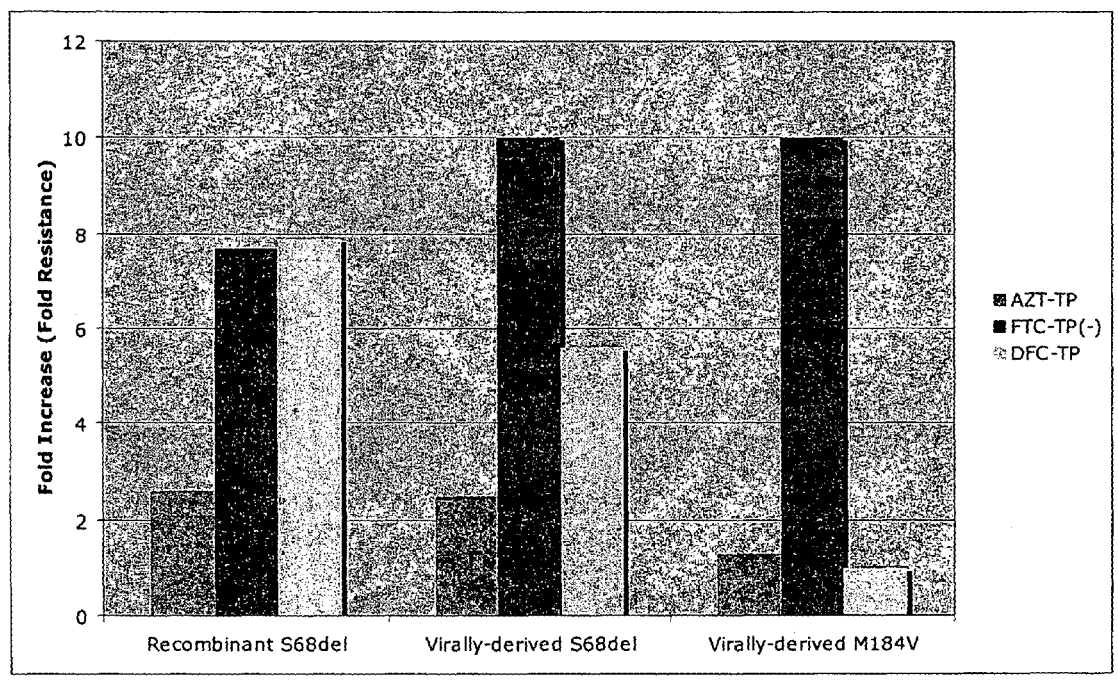
FIG. 6 is a graph showing the results of a heteropolymeric DNA colorimetric RT assay performed with recombinant S68del, virally-derived S68del and virally-derived M184V RTs. The recombinant S68del enzyme was tested in two separate experiments in duplicate. The standard errors for AZT-TP, (-) FTC-TP and DFC-TP were 0.1, 2 and 0.2, respectively. TP—triphosphate.

The resistance of RT derived from S68del and M184V particles against AZT, (−)FTC and DFC triphosphates was tested by a heteropolymeric-DNA colorimetric RT assay with 3.2 mM ATP. Fold-increases were measured relative to $HIV_{LAI}$ (FIG. 5). Both S68del and M184V RTs showed increased resistance to (−)FTC. Only S68del RT showed increased resistance to DFC (FIG. 5). RT from virally-derived S68del demonstrated a 5.6-, 2.5- and 10-fold increase in resistance to DFC-TP, AZT-TP and (−)FTC-TP, respectively, in the enzymatic assay (FIG. 6).

The level of resistance to NRTI-TP by the S68del mutants compared to wild type RT was determined as $IC_{50}$ values of RT activity in the absence of ATP (Table 6). Fold-increased resistance values were determined by dividing the $IC_{50}$ for the mutant by the $IC_{50}$ for respective wild type. The RT activity was linear during the assay time within the substrate range used, and thus steady state kinetics were assumed.

TABLE 6

| Reverse Transcriptase | DFC-TP | | AZT-TP | | (−)FTC-TP | |
|---|---|---|---|---|---|---|
| | $IC_{50} \pm SE^a$ | Fold-$incr^b$ | $IC_{50} \pm SE^a$ | Fold-$incr^b$ | $IC_{50} \pm SE^a$ | Fold-$incr^b$ |
| Wild type | 0.14 ± 0.02 | 1.0 | 0.27 ± 0.02 | 1.0 | 3.5 ± 0.3 | 1.0 |
| Recombinant S68del | 1.1 ± 0.2 | 7.9 | 0.7 ± 0.1 | 2.6 | 27 ± 2 | 7.7 |

$^a$The $IC_{50}$ values are expressed as µM of NRTI-TP. The $IC_{50}$ are averages from at least two separate experiments conducted in duplicate. The $IC_{50}$ values were determined using seven different concentrations of NRTI-TP adjusted optimally for each mutant's expected $IC_{50}$ value. Standard errors (±SE) are indicated.
$^b$Fold increase is calculated by dividing the mutant RT $IC_{50}$ by the respective wild type $IC_{50}$.

Enzymatic studies of the S68del RT detected similar resistance to NRTI-TP with and without ATP. Without being bound by theory, this result suggests that S68del resistance is not ATP-dependent and most likely occurs by enhanced substrate discrimination.

What is claimed is:

1. A method of evaluating the effectiveness of an antiretroviral agent on inhibiting HIV replication of an HIV virus comprising a codon 68 deletion in the reverse transcriptase coding sequences, the method comprising the steps of: (i) treating cells with an antiretroviral agent; (ii) infecting cells with an HIV virus comprising a codon 68 deletion in the reverse transcriptase coding sequences, wherein the deletion results in an amino acid sequence change from DST at positions 67-69 to DT; and (iii) determining the effect of the agent on HIV RNA production; wherein steps (i) and (ii) may be performed in any order.

2. The method of claim 1, wherein the antiretroviral agent is selected from the group consisting of DFC, lamivudine, emtricitabine, tenofovir, abacavir, and amdoxovir.

3. A method of evaluating the effectiveness of an antiretroviral agent on inhibiting HIV replication of an HIV virus comprising SEQ ID NO:7 in the reverse transcriptase coding sequences, the method comprising the steps of: (i) treating cells with an antiretroviral agent; (ii) infecting cells with an HIV virus comprising SEQ ID NO:7 in the reverse transcriptase coding sequences; and (iii) determining the effect of the agent on HIV RNA production; wherein steps (i) and (ii) may be performed in any order.

* * * * *